(12) United States Patent
Owens et al.

(10) Patent No.: US 6,780,610 B1
(45) Date of Patent: Aug. 24, 2004

(54) IDENTIFICATION OF A SMOOTH MUSCLE CELL (SMC) SPECIFIC SMOOTH MUSCLE HEAVY CHAIN (SM-MHC) PROMOTER/ENHANCER

(75) Inventors: Gary K. Owens, Earlysville, VA (US); Cort Madsen, Robinsville, VA (US)

(73) Assignee: Setagon, Inc., Charlottesville, VA (US)

( * ) Notice: Subject to any disclaimer, the term of this patent is extended or adjusted under 35 U.S.C. 154(b) by 0 days.

(21) Appl. No.: 09/600,319

(22) PCT Filed: Jan. 15, 1999

(86) PCT No.: PCT/US99/01038

§ 371 (c)(1),
(2), (4) Date: Jul. 13, 2000

(87) PCT Pub. No.: WO99/36101

PCT Pub. Date: Jul. 22, 1999

Related U.S. Application Data

(60) Provisional application No. 60/071,300, filed on Jan. 16, 1998.

(51) Int. Cl.$^7$ .......................... C12N 5/16; C12N 15/63; C07H 21/04; A01K 67/027
(52) U.S. Cl. .................... 435/69.1; 435/325; 435/320.1; 536/24.1; 800/13
(58) Field of Search ............................ 435/69.1, 320.1, 435/325; 536/24.1; 800/13

(56) References Cited

U.S. PATENT DOCUMENTS 5,665,543 A   9/1997 Foulkes et al.

OTHER PUBLICATIONS

Miano et al., Smooth muscle myosin heavy chain exclusively marks the smooth muscle lineage during mouse embryogenesis, 1994, CIRC. RES., vol. 75, pp. 803–812.*
White, et al., "Identification of Promoter Elements Involved in Cell–Specific Regulation of Rat Smooth Muscle Myosin Heavy Chain Gene Transcription," J. Biol. Chem. Jun. 21, 1996, vol. 271, No. 25, p. 15008–15017.

Kallmeier, et al. "A Novel Smooth Muscle–Specific Enhancer Regulates Transcription of the Smooth Muscle Myosin Heavy Chain Gene in Vascular Smooth Muscle Cells," J. Biol. Chem. Dec. 29, 1995, vol. 270, No. 52, pp. 30949–30957.
Katoh, et al. "Identification of Functional Promoter Elements in the Rabbit Smooth Muscle Myosin Heavy Chain Gene," J. Biol. Chem. Dec. 02, 1994, vol. 269, No. 48, pp. 30538–30545.
Madsen, et al. "Expression of the Smooth Muscle Myosin Heavy Chain Gene Is Regulated by a Negative–Acting GC–Rich Element Located between Two Positive–Acting Serum Response Factor–Binding Elements," J. Biol. Chem. Mar. 07, 1997, vol. 272, No. 10, pp. 6332–6340.
Madsen, et al. "Smooth Muscle–Specific of the Smooth Muscle Myosin Heavy Chain Gene in Transgenic Mice Requires 5'–Flanking and First Intronic DNA Sequence," Circ. Res. May 04, 1998, vol. 82, No. 8, pp. 908–917.
Zilberman, et al. "Evolutionarily Conserved Promoter Region Containing CArG–Like Elements is Crucial for Smooth Muscle Myosin Heavy Chain Gene Expression," Circ. Res. Mar. 23, 1998, vol. 82, No. 5, pp. 566–575.

* cited by examiner

*Primary Examiner*—Anne-Marie Falk
*Assistant Examiner*—Daniel M. Sullivan
(74) *Attorney, Agent, or Firm*—Townsend and Townsend and Crew LLP

(57) ABSTRACT

The present invention generally relates to promoters, enhancers and other regulatory elements of smooth muscle cells ("SMC"). The invention also generally relates to the use of these promoters, enhancers and other regulatory elements of SMC to create animal models to study SMC physiology and pathophysiology. The invention further relates to a smooth muscle myosin heavy chain (SM-MHC) promoter/enhancer element which is capable of conferring SMC-specific gene expression in vivo. The invention also relates to methods for the targeted knockout, or overexpression, of genes of interest within smooth muscle cells. The invention further relates to methods of conferring smooth muscle cell specific gene expression in vivo.

8 Claims, 17 Drawing Sheets

Figure 1A:
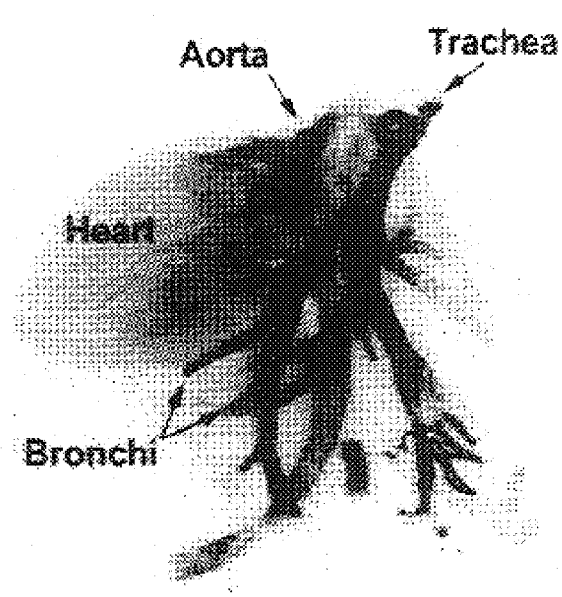
Figure 1B:
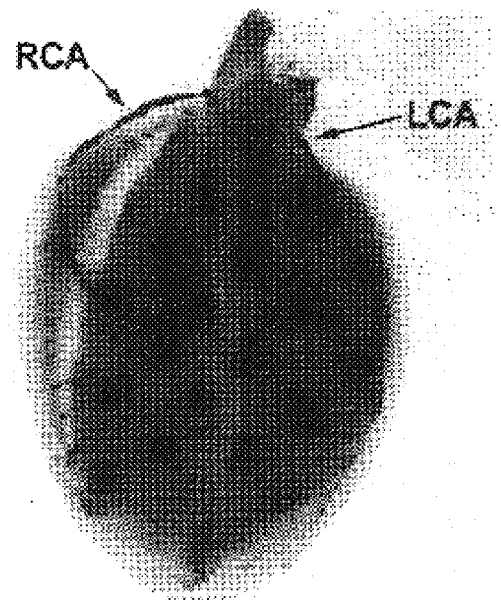
Figure 1C:
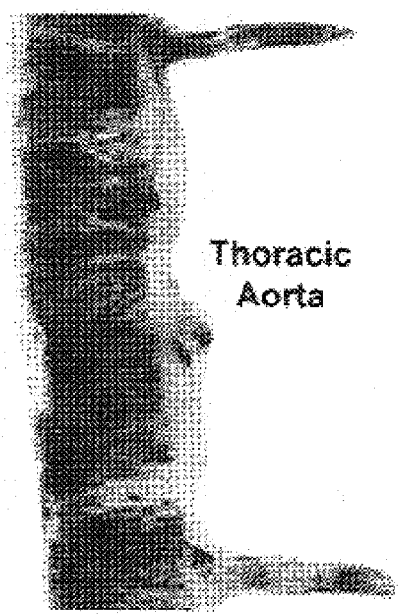
Figure 1D:
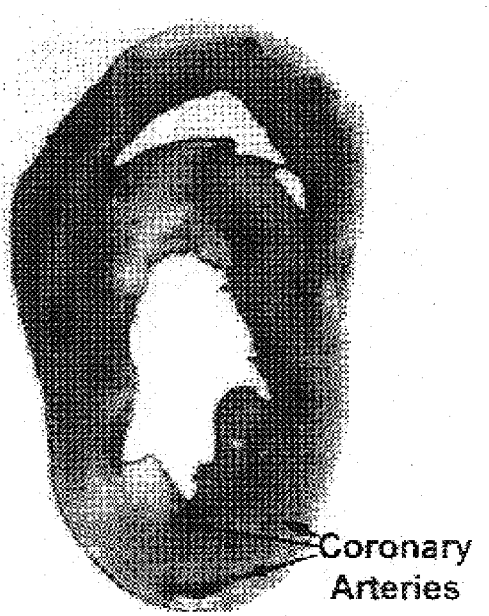
Figure 1E:
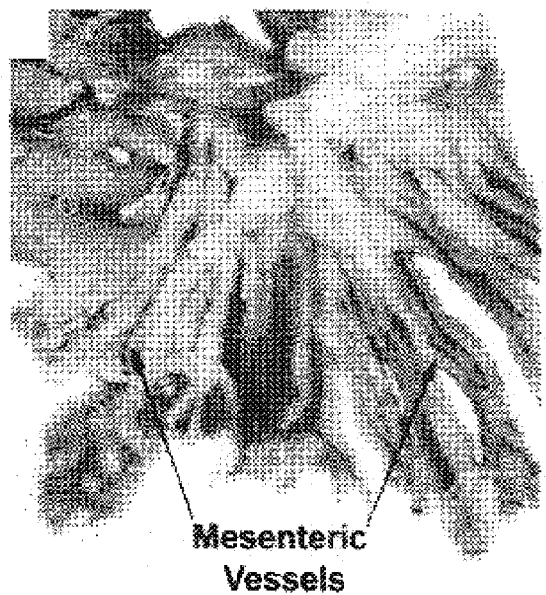
Figure 1F:
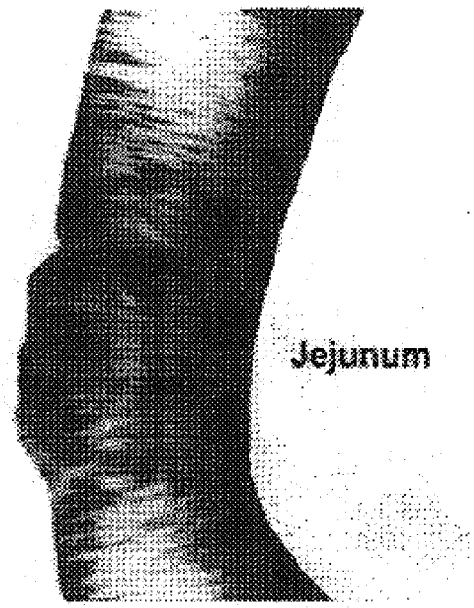
Figure 1G:
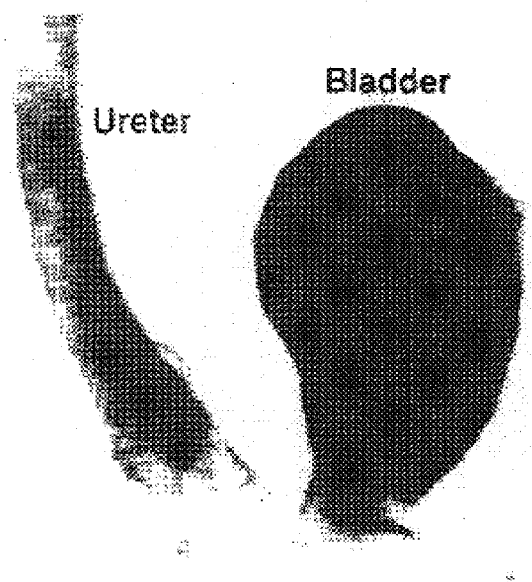
Figure 1H:
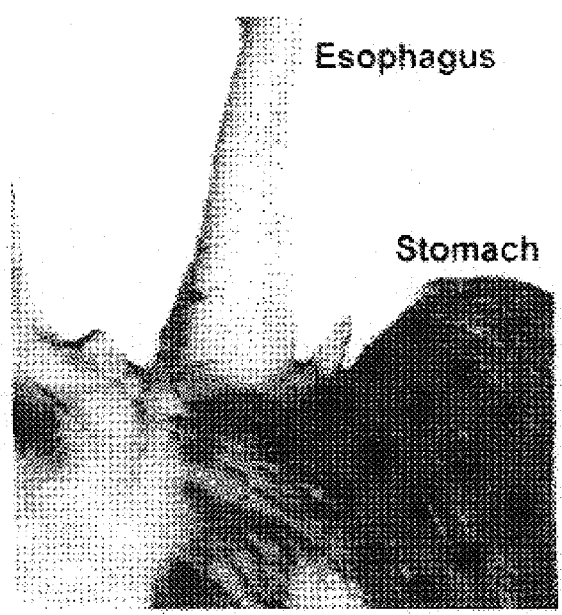
Figure 2A:
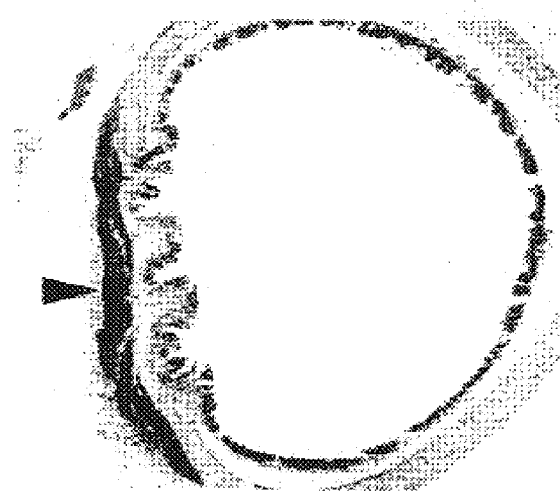
Figure 2B:
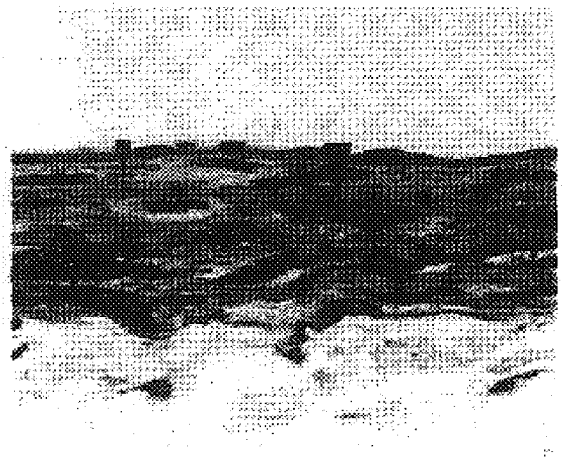
Figure 2C:
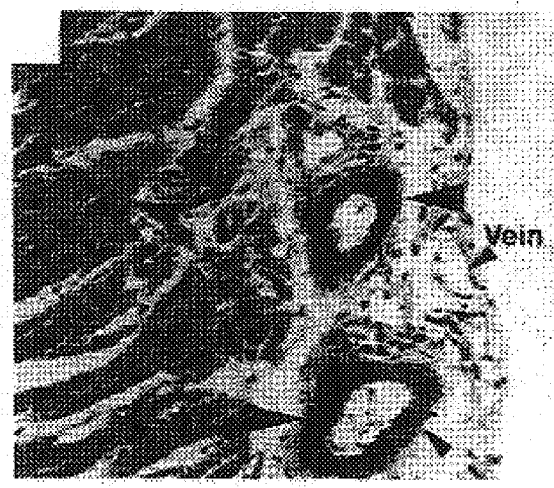
Figure 2D:
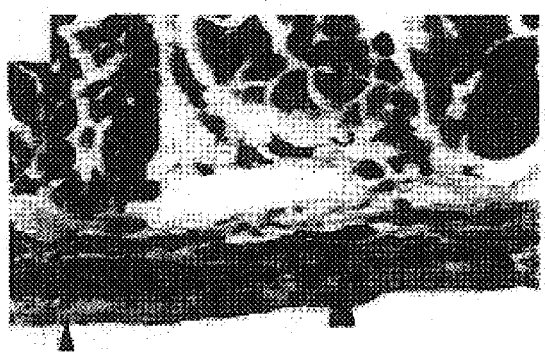
Figure 2E:
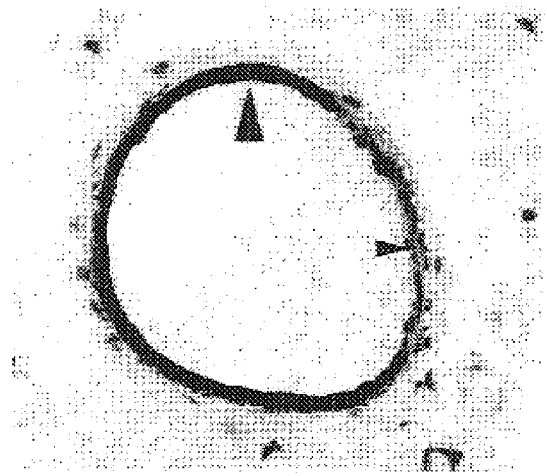
Figure 2F:
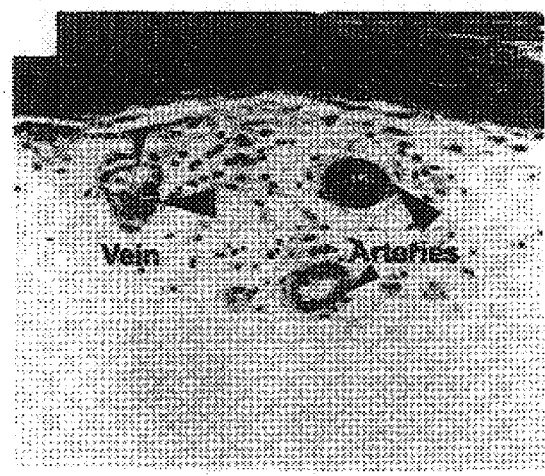

RAT SMOOTH MUSCLE MYOSIN HEAVY CHAIN GENE SEQUENCE (−4,216 TO +11,795)
NUCLEOTIDE 1 CORRESPONDS TO −4,216 bp RELATIVE TO THE SM-MHC TRANSCRIPTION START SITE

```
AGATCTTAAA ACACATCAAC CTGGGCTGAG GGGATGTGTG TCTCTGTGTC TGTGTATGCA   60
CATGCATTTG AGGCCAGATG AAAATGTCAG ATGTCCTCTC ACTGCTTTAT TCCCTTGAGA  120
CAGGGTCCCT CACTGAACTT GTTGGAGCTA TGCTGGTAGC CAGCAAGCCC CAGTGGCCTT  180
CCTGTCTCTA TCTCACACAG CACAATATGT GTGGCCATGC TCCACTTTTT TACATGGAAA  240
TTGGGGTCTT CCAACTGGGG TTCTCATTTG TGCAGTGACA CTCTTCCCCA CTGAGCCATC  300
TCCTCAGGCC AGCTGATATA TTTTTAAATA ATTAAATATT TAGCACATGC CTTTAGAAGC  360
CAATAGCTAT TTAAAGCTGT TTGCTTAAAA AAAAAAAAAA AAAAAAGACT TCATTATCCC  420
AACACTTATG AGGGAGAGAC AATAATTCCA AAACCAGAAC CAGCCAGGGT ACACAGTGAG  480
ACTTTATTTA AAAAAAAAAA AAAAAGAAAG AAAGAAAAAA AAAAGAAAAA GAAAAAAAAA  540
GGCTCCAAAG AGAAATTTCC CCTTCATCAT CTAATCACAA GAAAACAATT TATTTATTTT  600
GACATCACTC AGTCCAAAGG AGCTTTTTGT AAAGTGACTT CTCTTCTTAA AATAAGTGAC  660
CCTTCCCAAC CACCAAAAAC AAAACAGAAA CCTCTGCCCT GTTCTAGAGT CCTTTTGAAG  720
ACTTCAGATA CCTGAAGAGT GGACAGATAT TTACCGAGTG ACTTAAATGA ACATACTGTC  780
CCTGGGTACT GCTCAAGCAT GCCAGGAGAG CATGGATGGT TTATGCAAGG CTGGCACTGT  840
CATTAACAAC TCAGTAAGGC GGAGAAGACA GAGAGCCTCT CCTAAGACAA TGGCACATAA  900
GGACATGGGT AACCCCAGAG GTTCCCGGCT AGTACTTAGC AGAGCTGAGA TCAGACTTGG  960
GCCTCTGTGC TCGCTTGCCT AGTGGGCAAC ACTCAAGACT GGGGTAAACA ATAAGTTGAT 1020
CTGGGATATG GCTCAGTAAT CACACTGAGA ATTCAACACT GGGAAGGCAG AGGAGGATCC 1080
CTGGGATTGC TGCCTGGCTC TCTAGCAGCC TAGCAGAATC AACAAACTCC AGGTTCAGTG 1140
AGAGATGCTC ACAAAATAAA ATGGAGGAGC AACTGAACAC ACTCAGTGTT GACCCACACA 1200
CACACTAAAG AACACGTGTA CCACACAGAC ACAGACACAG GATAACCTAC CCATGTTGTG 1260
TATGGACTCA GCCAGCCCAG GTTGGAAACT CAGTTCCTCT GTTAACTCTT TTCAAACCTG 1320
GGTCCTCAGC GATGTGCTGG GGAACCTACT TCACGGCATT ATTCTGGGCA TTAGATGTAA 1380
AGGAAGCAGT AAAGTTTCCC TTTTCTTGAC TGAGGTGATG CGAGAATGAG GGCCTGAATT 1440
CCATCTCTAG GACTCACATA AAGACACCCA GACTGCACTG GCCAGTAAGC CTCACCTATG 1500
CCTCCAAGCC TGGCTGTGAG AGACTGTCTC AAAAACAAAG TAAAAACAAC AAAATCAATG 1560
TCAGATGTGC ACACATCGAA TCCCAGCATG TGTACGGCAT GCTTGCAGTC AGCCTTGTTT 1620
ACAGAGAGTT CTAGGCCAAC CAGCTATACA CAGTGAGACC CTGTGGTAGA CGGCTCCTAA 1680
GAACTGACAT TTGTGACTGA CAGATGTGCA CATCTACCAC ATGCACATCA CAGTTTCCAT 1740
TTTACAAAAA GGTTAACACT TACTAATTGA TTAGGGAGTG GGGCACCCCA CTGCTACATG 1800
TGAAAGCCAG AGAATGATGT GTTCCAGTCG GTCAGTTGTG TCCTTCCACC ATGTAGGTCC 1860
TAAAAATGGA ACTCAAGGCA GTCTTGGCAG CAAGTGCTTT ATCCATAGTG CCATCTTATT 1920
GGCCCAGTCT CCTTATAATG AAATTATTTG TGTTTCCAAG TTGATGTAAT TCTTTAAAAA 1980
TCAGCTGTGC TCCTTGGAGT TTGACTTCAC TGAAGCCTGC TACAGGAGTG CCCTTCCTTC 2040
CTAGCACTAG GATGCCAGC  TCTGGGCTGG TTTCAGACTA GGGTAGGTGC AGGTGGGCCC 2100
TGGGCTTCCC TCCTTCATTC CTCCTGGGCT CAATGCCAAG CCGGTTTCCA TTCCTTTTAC 2160
GTGCACTGCG AAGAGGCTTT GGGGAAGCGG CCTCATCCAT CATGCAGAGA GCTCCTCCCC 2220
CACCTCTACA GAGAGCCAGC CAAGCTGCTG TCCTTGGCTC TGCTCTGTCC ACCCTGTGAG 2280
GAGGCTGGGA TGAGGTTGGG GATGGGGAGG ATCAGGATTC AGATGTTTTC AAGTCTGAGA 2340
AGCAGGTGAG CTTGGTCCTA GAAGAATATG GAAGGGGTCT ACTGGGGTTG AGATATAGAT 2400
CACTGTATCA AAGTCAACAG GGGGGCTGTG TGGCTTTTTC ATATCCCAAA GTCAGCTTGG 2460
TGCTGGTTTC CTAGGCTTCC TGAGTCCGAC AAAGGTGCAG TGTGTTAATC TCACACCACT 2520
TCAAGGACTG TTACAAAAAA AAAATAGGAA GGAGCTCGAT TCGCCCCTTT TTACAGGCAG 2580
GGTAACTAAG AGCCAGTACT TGCCCATGGG CCTGCTGTTA TAAAGAGGCT CAGTAGACTC 2640
```

FIG.8A

```
CCATTCAAAC AACTGTGCTC AGAGGCCTTC TGTCGTCCTG TGGCCAATTC CCCTATTGCT 2700
CTCTGGAGTG AATATTGGGA TATTAAACAG TACTGACCTT GCTGAGGACC CTCAGGGTAC 2760
TCAGCTCTTC TGGCCTGCAA AATGGGGCTG GGACAGGTTG GCCAGGATCA TCCTCTGGTT 2820
GGGAGAACCA GCTGCACGTG GGTCTGGAGC TCTTATTAGT ACTGGGGTCC CCATAACGCT 2880
CCATGGGCTC AGCGGGAGGC TGCACGGGAC CATATTTAGT CAGGGGGAGC CAGAGCCCCG 2940
CTGGTATGCC AAGCTGGGAA TTCTTGTTTC GAGAATTGCG CCTGGCCTTT TTGGGTTGTT 3000
TCCCGCCCAG GCCCAGGAGG GAGGACCAGC TCAGGACCTC GAGGGTCCGT GCGCGGGAG 3060
CGAGGCGTCC CCGGCCTGGC ATGAGGCCAA CTCTGCCTCG ACTTCCTTTT ATGGCCTGAG 3120
TGTGAGTGCA TGGAGAGTGG GAGGGAGGGA GGGAGAGAGG GAGGAAAGAA AGCGGGGTGG 3180
GGGGGTGGGG GGGTGGGGGG GTGGGGGGGT GCGGAGAGCA GAGACAGAGA CAGAGAGACA 3240
GAGAGACACA CAGAGAGAGA CAGAGAGACA GAGAGACACA CAGAGAGAGA CAGAGACAGA 3300
CACACACAGA GAGAGACAGA CAGACAAAGA GAGAGACAGA GACAGAGAGA CACACACAGA 3360
GAGACAGACA GACAAAAAGA GAAGAGAGAC AGAGACTTTA GGGACGTAAT CATCACAGGG 3420
AAATCAAAGC TAAGAGTGTG ATGAAAAGAG TGTCAGGTCA GACAAAAGAG ACAGGGGCCA 3480
AGATCCGTAC AGGGCTAAGG GACACAGAGA TTGAGAACAC CGAGTGGTAA GGGGGGCAGC 3540
TGACAGCAGG TCCCCCACAT TCTCTTAGAG TCTTAGCATG CATCCTCCAA GTGCCATAAC 3600
GCAGTAGCAA CCCGCTTTTC AACGATGCTC AGAGAAACCA TGTTATTGGT CCCAGGCACC 3660
CCGGTTGTAG GGTGAAAGGA GCTGCAGAGA ACAAGTTGGA AAAACAAGTT TCCCAGCAGT 3720
CACAGAGGAT ATGCAGTGAC TGTGCCGACT TGTTTTTTTT TTTTTAAGTC CCCTTCCCCC 3780
CCCCCGCCCC GCCCCCGGCT TGCTAAGCAC AACCGGCTTC GAATCTTAGG AAGTGGCAGG 3840
CGAATGAAGA GGGGATGAGG GAGAGAGGGT GGCATCAAGT CTCCAGTATG TATGAACAGA 3900
AAGAGGTTAA AATCCAGCTG GAATGGACCT AGGGGAAGAA ATTCTCAAGT CTCCCTACAG 3960
ACTCTGAACA CCGAATCCCT TTTCTCTAAG GACGCAGGAT CTGGGTGGCT GCAGGGAGCG 4020
AGGCCTGAGG CTGTGGGTCA ACTTGCCAGC AGCCCCCTG CGCCTGCGCT AGGTGGTTCC 4080
CAGAGGCTCT GTTCCTCACC TGCAGGGGGC GCTGGGAAGG GCAGAGGACC CTCCCACCCC 4140
GCCCGGCAGT CACCTCCCCT TCCCCACCCT CGGGTAGCGC TGACTCTATA AAGCCAGATG 4200
                                   ┌─ TRANSCRIPTION
TCCGAAGCAT ACAGAGAGAT TTGGACCATC CCAGCCTGGG ATCAGTGTCA GATCCGAGCT 4260
CTCCATCCGG TGTTCTCCTG CTAGTCCACC CCAGTAGCAG ATCTGTAAGT AGAAGTTGAT 4320
CCTTAGGGGG CAAGCCTGGG CGGTGAGCTT GAGCAGCTTC TAAAACATCC TCCAGGGAGT 4380
GGGGACCCCA AGGGGTTCTG ATTGTCATCT CTTATAAGGA CAGTGGGAAG AAGCCCGGTA 4440
CAGGACCACC CTAGACCTCC CGTGATTACT CCCATTCTCC GCACCAAACC AGCATCCTCA 4500
GGTTGCCTAT GAACAGAACC ACCTGGGAAA GTGGGGTAGG TAATTAAAGG TTCTGGCCAC 4560
TGGGCCCAAT TCCAGGTATT TTAAGACTAC AGTCTAAAAA GCAAACAAAA TGGCCTACTT 4620
AAAAACTAAC TAGTGACACA GTGGACAAGT GAACTGTGGT GGAAACTGTG GGTCTGAATT 4680
CAAATACCAG TATTGAAAAT AATAAGAAGT CTGGGATAAA TATCCACTGA ACATCCCCAG 4740
AATACTCAAA ACATGGGTTA AAGTTTAATG ACTCTGAACA CAGGCCGTGT GTTCTTATTC 4800
CACTCCTAAT GGAATGTGCT GTTGAAAATT TACTGGTAAA CAAAAATGCT TAATGTTAAA 4860
TAAGGTCGTT TCTTCCTCTG TTACTTCCAA AACACAAATC TCCATTAAAA AGGAACCTTC 4920
TCCAGTTTGG TTGGGCCCCC AGATGCCCAG GTGGGTGCTG AGGCTCCATT TGCATCCCCC 4980
ACACTGAGTG AGCAGACGAT GGATTTTGGG GCTCCTCAGT GGGAAGGTTA CTCTCAGGTC 5040
AGGGAGAGGA GCTAGCAGAG AAATTTATGC TATTCCAGTT CAGAATTGGA GAAGTCTTGC 5100
CATGTCCAGA AAGCACCCTT CAAAGTTATG TCTGTCAGAG AACAGAAAAA TTTTTTTTGA 5160
AAGCCAGGAC AAGGCTGCTT TGGTTCTACT ACTAAGAACT GAAAAACTGC TGACTTGCTG 5220
```

FIG.8B

```
GGAAAGAAGG AAATCCGGTT GTGTTTGGTA AACTACTCTG CTTCGTTGGT TTCCTGGGGG 5280
AGGTTTTTTT TTAGTTCAGT AATTCAATAT GCTATTTAG ACTCAAAGAA AGACAGGTCT 5340
GAAAGTCTCT CATAACAAGA AACACTTTCT CTTTTATGAT GTTGTTGATG GCACACTTAA 5400
CAAGCCAGGT GCTTTAACAG CGTTTAGATG GAACTGGGTT CTTTTAATCA TCATATACAC 5460
CTTACCTTGT CTTGACATCT CTGTTTTTCC CAAAACCAAA ATTTGTTGGA CTCCTGTTTC 5520
TGATGGATTC AGTGTTTCCA GCTTCCATCA CTTTTGAAG AAGATTGAAA CTGATCTTTT 5580
ACCAATTTAA AATGACAGAG ACTGTCTTTT AAATTTTGTT GATGTTGTTG TTTCCCTGTG 5640
GATGTGGTAG GGTTCCAGGA GGCTGGCGTG ATCTCAAACA TGCCTGGGCC AAGCCACCCT 5700
GGAGAAACCT GGACTTTTAT TATCAGATCT GAAATAGAGC CTCTTCCGTA CAAGGTAGTC 5760
ACTATGGATT TATCATTACT TTTCTGTGGG AGGCTGGGCT GGAGGCAGAC ATGCCCTTGT 5820
ATGGATGTGT TTTCTATGAG GCCATTCCCA GTCCCCCTTG GCCAATCACC CAGCCTTTCG 5880
ATGCAGCCTG ACTGGCTTGA GTTCTGGGTA CTTCTCTGTC TTTCCCTGTA GAGATGGACA 5940
ATGAAGTTCT TTTTTTCCTC TCTTTTCTTG TTTGGAAGTT CTATTTGTAT TTTTTTGGTG 6000
GAAATTATAT TCCACATATC TAATAAGAAC GGGTGGTGTT TACATCTAAT AAACCATTGA 6060
ATAATTTTGA AACAGGATAA AGACGATCCT TTTAGAAAAC TATATCCCGT TCAAATACT 6120
CAGAATCAGG TCTTAACCAC ATTATTTTGC CAGGTATGGT GGCTTGTGTC TAAAATACTA 6180
GCACTTGGGA GGCTAAAGCA AGAGAGTTTG AGGCTAACCT GGACTGCATA GCAAGTTCAG 6240
GCCATCCTGG ACTACAGTGG GAAACACTAT CTTGGAAAAA ATAAAAAATA AAATCAAAA 6300
CCCAGCCTAA TGGTACATAA CTTCAATTCC AGCATCTGAG GTAAACCAGG AAGCACAGCT 6360
GATTAATGAA CCCAAAGTCA GCCTGGGCTA CCTAAGGAAT CCTATCTTTT ACAATTTGTT 6420
GATGCTGTTG TCATTTTCCT GATCACTTTC CCATCTGCAG AATGGGACTG TTGAGAACAG 6480
CCAGCGTGTT AATGTTTCTG TAGCACTTGC TTAGTCTTCT GAGAAGTAGA AGATCACTTA 6540
GCTAGGGTTT GATCCCCATG ACTGCAGCAA AAGAGGAAGA CTCATTAATT GGAGTCTTCA 6600
CAGTAGCCCT TGGAACCAAT ACTAATAGTC TTCACTCCAT TTCATAAATG TGGGCTTTGA 6660
AAACTTTGTT CTGTCTATAA AGATGGGGG CTCTTACAAA CTAAGCTTCT TGTAACTCCA 6720
GAGCCTAATG CCCTTTTGGG AGCTTTCAAT AGATAACCCA TGTGAAGGGT CTGACACAAG 6780
GCTGGCACCA GCAAAGTTCA GCAGATGGTA ATTTATAGTA ATATGACTAG GGACGCTTAA 6840
GAGCATATTC TGTATGACAC AGCTGATATC AAGAAACCCA AACGGTGGCC TTTCCCCTAA 6900
AGCAGAAACT CACCCCTAAT TTTCCTTTAG TGTAAATCTC ATAGTGGATT CTTTGCTCCC 6960
TGGTTCTCTT TCTGTCACTA GTGACCTTTT AGTTACATTG ATCTATAGGC TTCAAGGACC 7020
AGGAGGCACA GAGTCAAGAG AAAGGCAAGC AAGAATTTGA AGGGAGAAGG AAACCGCTCA 7080
GCACTGTAGC AAGGGGAGGT CAGGCTACCA TGATGCTCCT GCGCTTCAGG GAATTATCCT 7140
CTCAGAATGG CCAACAGGGT AGGGACCTGG CCTGTTCCAC TCAGGCCCAT TTGAACTTTC 7200
TTTCTGTTCT ATGGGTCCCT ACAGATGAAT TCAGCCCACT GTAGACTGGA AGTTCATCTT 7260
TAACAGCATC CAAACGGAAC ACATACAGAC CTTCTTTCTT GTCACTGTCC CTGAGTCAAG 7320
CAGCATAAGA ACTATGTCTG CCAACCTGCG AGGGGAAGTT GCTCAAGATG CTATGCAAAC 7380
ACTCCAGCTT TCCATGGAAG GGACTTCAGC ATCTATGGAT GGTGGTAGCA AAGCACTCCT 7440
CAAGCTGATC AAAGAATAGC TGTCCCTTCC TGCCCCTCCC CTAATGAAGC GTGCAGTCAG 7500
TGACAGAGAC CTCAGAAATG TCTTAGGTCA CCAAAGGTCA TTCTTGCCAT CCCAGGCTCC 7560
AGATTAGCAT TTTCTCCCTT TTTATTTCCC TCCATTTTGC CTGTCTGCAT ATGCACTACT 7620
AACAAACATT CTTTCTTTCT TTTTTTTTTT TTTCTTGGAG CTGGGGACTG AACCCAGGGC 7680
CTTGCGCTTG CTAGGCAAGC GCTCTACCAC TGAGCTAAAT CCCCAGCCCC GCTAACAAAC 7740
ATTCTTAAAT AGAATTCTAA ATTTTTTAAA GTCAAATTTC CCTTTTACTC AAACCCTGCC 7800
ATTTTACAAA ACATTTTTCA CCTTATCACA AATCTTCACT ATCTTTTCTA TATCTTTATA 7860
```

FIG.8C

```
TCATTGTATG TTACTTTTTA TCTGCTACCT AGTATTCTGT TACGTATTTA ATAAAATATA  7920
CTTGGTGCAT GATGCCATGT ATAAATGGCG CTTGGGGAAG TACCCGTGTA CTAGTTGACT  7980
GTTGCCCATC AGAAATGCCC AGGACCAGAA ATGTTCCAGA GTTTTCTTTT CTTTTAAATT  8040
CTTTTTGATT TTGGGATATT TGCACATAAA TAATTATATA TTTGTATATA AATAATGATA  8100
TATCCTGGAA ACGAGCACTA ATTCTTTTGT TGCCTGTCTT CTGGGTTTTT TTTTTTTCTT  8160
TCCTTCTTTC TTTTTGTTCT TGGCCATCCT GGAGCTCTCT GTAGACCAGG TTGTGCTTGA  8220
ACTATAGAGA TCCTCCTGCC TCTGCCTCCC ACATGCTAAG ACTAAAGGCA AGAGCCATCA  8280
CACCCATCTG TGAGCACAAA TCTTGATATT TCACCTTTGC TTTATACAGA TGGTTGTATA  8340
GTCAGTCGTT GTATTCGATG TTTTTAATTC TACATTTTCA CTGTGACCTG CTACATGAAA  8400
TTCAAATACA AACTTGTCCA CTCACACAAT ATTGGCCCTC AAAAAGCTGT GAGCCTTTGA  8460
ACTTTTGGGG TTAAGAATGT TTAGCTTGTA TCCGTATTCT TCGCTTGTAA ACTCTCTTCC  8520
TGTAATCACA TGAGTTCCTA GCAAAGAGGT GAATAGATAG CACATTGGGA ATCAGCATCT  8580
GTCTCTAAAT GGTCTTTGAA AGAAACTGTA GATACCTGCC TGGACCAGCC AGACCTGTGT  8640
CTTAGCACCT ATTTTAAACA TTGTTCTACC TGAGTTGTAA GATGCAAAAC ATAGTGGGGC  8700
TCTGAGGGCC CAAAGGCCCT GAACAGGGGT GACCTCAGTT GTGTGGAATA GGGAGAAAGA  8760
CAGCAGAAGG AAGGGAGGAA AGACGGGCAA GGAGGGGAAG GTGTTCATGT GTATGGCTGC  8820
ATCTAAATAG AAGCCATGAA GACTAGCTAT TGTTTCTCAG GTCCTTCCAA CTTGCTTTTG  8880
GAGACAGGAA CCCTCACCAG CCTGGAACTT GCCAAGTAGC TAATTGGCTG GCTCTTGACC  8940
CCTAGATCTC TTTCCCCTCC ACTCTAACGT TACAACATAC AGCTCTCTCT CTCTCTCTCT  9000
CTCTCTCTCT CTCTCTCTCT CTCTCTCTCT CTCATTTTAT TTTTTAAAAA AATTTATTT  9060
ATTTATTTAT TTATTTATTT ATTTATTTAT TTATTTATTT CATGGATGTA ATACCTGTCC  9120
TGTCTCAACC CCAAAATGGG CATCGGATCC CATTCCAGAT GGTTGTGAGC CACCATGTGG  9180
TTGCTGGGAA TTGAACTCAG GACCTCTGGG AGAGCAGTCA GTACTCTTAA TGCTGAGCCA  9240
TCTCTCTAGC CCTTTCCCCC TCTTCTAAAA CATAGTTTTT GAAGATCTAA CGCAGATCTT  9300
CAAGTGTCAG TATGGCAAGC ACTTTGCTGA CTCACCAGCC CATGACCTTC TCCCTTAATC  9360
TCCAAATCCT TTTAGTGGGA GAGACACAAT CGTTTTACTT TAGCCATTGG AAAGAGCTTC  9420
CTTCTAAAGC AGCTTGAAAA GCCATTGGGG TTTCCAGCGT GTGTGTGGCA GTGTTACCAG  9480
GTTATTGTGA TGGGACAAGT TCTTATTCTC TTTCTTCTGA GGAGGTACCC TGGAGACCTT  9540
GGGAAGTGG GGGTGGTAGG GAGGTTTATG GCATTGGGGC AGGGAGTGAA AAGAGATTT  9600
ACTGCTGAGA GCAAAAGGAT TGTTAGATCC AACAATCTAA CAAAAAAGGT CAAACTTTTT  9660
TTTCTTTTAT GACCTTAGTT GTGATAACAG AAAAATAGTA ATGTAAGTGA TGTCCACTTC  9720
ACAGAATCCT CATAAGATAT TCAAGACCAT AAATGTGGGC CACTCTTACT TTGATGCCCA  9780
GTAGGGGGCC CCTGAGCAGA TGCAGCTTAG TTAATAGGAT GCTTGCCCAC CATGTTTTGT  9840
ACATGTTCCA CCCTCAGTAC ACAGCCAGGC ATCGTAGGAA ACACTTGTAG CCCCTAGCAC  9900
TTGGCGGGAG GACCAAGAGT TCAAGTCCGT TTTTGATTAT GTAGTGAGTT CAGGGTTAGC  9960
ATGGGCTATA GGAGACTGTA GAGGGCTATG TGATTAAGAA CAGATTTGAG CCCCACAGGG 10020
CTCCTGGTGC AGCATGAGTT TGAGGAACTA GTGTGTATAG CATGCTTTTC CTTCTTCTTG 10080
GTATGTCAAG TGACTTTCTA GACGCAGATG TGGCATCGAA CTAGAACTAA CATTATTGGG 10140
GCCTCTTTGG ATTGCTTACT GAGCTGCAGC TTTGGCTCCA AGAACTTATT ATGGAGATGG 10200
GCATGGTGGT AACAACTACA CTACAGAAGA CTACTACTTT GAGACCAGCC TGTACCAGAG 10260
CCTGGTGGAT ACAGCTCAAT GGGAGAACAC ATATTGAGCA TGTACAAGTC CTGAGTTCGA 10320
TCTTCAGTAC CTCGAATATT GGCCAACTAA AAGGAATGAA TTTAGGGGTG GGAATAAAGT 10380
TCAGATAGTA GAGTGTCTGG CTAGCATTCA CAAAGCCCCA AGTTTGACCT CCAGCACTCC 10440
AGAACCTGGA TGTGGTAGAG TACATCTATG ATCCCAGCAC TCAGGAGAAC TTCAAAGTTA 10500
TTCCAAGCTA CATAATAATA CAAGACCAGC CTGGGCTACA CAAGATCTTA TCTCAAAAAG 10560
```

FIG.8D

```
CTTTGGTTTC AAACTGGGGA CAGTTTTCCC TCTGGGAGTG ATATCTAGCA GTGTCTGGAC  10620
CTCCTTTTGA TGTCATGACT AGGAAATGGT GGATACTGGC ATAGAGTGGG CTGAACTCAC  10680
ACTGAACAGC ACCAGAGAAC CAGCCAGTGC CAAGGCCAAT AGTACAGGGG CTGAGAAAAT  10740
CCACTGTAAA TCAGGAGTCA GAACAGGACC AGGAGTTAGA AAACCAAATG TTACTTCAGC  10800
CTGTCTTGTG GGTCTTTAAT GGCATTGTGA TTTTGGTTCT AGTCATCATT TCTTTTCGGT  10860
ATTGAGATTT GAACTAGGGT CTTGTGCATG CTAAGTAAGA ACTCTGCCAC TGTGCCATAT  10920
CCCAACCTAT GTGGTTGTTT TGTATCAGGG TCTCTCCTTG TAACCCAATA CTCAAACCCA  10980
TCATCTCCTT CATCATGGGA CTACATATGT GAGCAGTTTT ACTGTTTTC CTTCTTCCTT  11040
GTGTTTTACG CAATACCTGT CCTGATATTT CTTGCTGTAT TGTCACTGTC CCATCTTTTG  11100
AAAATTTCAG GCTCTGAACA GAAATGAAGC AAATCTTCTG ACAGTAAATG GAGTTCCCTG  11160
AACTTCCAAA CTGCCAGACA GAAGCAGAAT GTGTCCTCTG TATGCCTGTA ATTTTTTCTG  11220
TCCTTGAGTT CTCTGCCTGC CTCCTCTAAA TTCTAAAAAA AGAAAGAGCA AAAACAAACA  11280
GACAATAAAA AAACTTGCAA CTTTTTTCAG AAGCCACAAG ACTGTAAAAG GACCAACAAA  11340
CTGCTTTGCC TCTGTGTGCC TTGGTTTCTC ATTGGTAAAG GAATGGTAAC ATCTTTCCTG  11400
GGTTGTTTTG CAATGCTGGG GATAGAATCC AGGGCTTAGA GTATATTAGG TTCCCTGCCT  11460
CTAAACTATA TTCTCTAGTC TTAAAAGTAT TGTTTGCATT GTTACTGTGT TTTATGGTGG  11520
GGGGATGGGA ACCCAGGGAC TGTAGCTTAC TAAGTGTTCT GCCTGTGGGC TATACCCTAG  11580
CCACCTCCTA GGACTTTGCT GTTTATTTAT TTATTTAGTT TAGGGCTTTG TTATTGATTT  11640
ATTAGTTAGT TAATTTAGGG GATTAAATGA GAGAGTAATT ATTACCTCAT ATGGTTTAGC  11700
AACTATTACA AGCATGCTAG TATCATTAAT TTGTGGGACT CTGAATTCTT TCCAAGGCAA  11760
GTGTGTGTCC AGTATTGTTC TGGGAACCCC TCCTTCCCTG CAGGTTCATA GGAGCAGAGT  11820
GGTTTTCTGG TTGTAAAATC TGCCAAGAAC TGGAATGTCC TGTCTAGGCT CTGCATCTTA  11880
GTGATGGGCA AAAAAGATGT AGTGTGTGTG ACATTCATGT GGTGGTGCAT GCATGTGTG   11940
ACATGAGTGT ACATGCTTGA GCCCTGAAAC AGGATTTCTC ACTCAATTGC CATCAAGCTT  12000
TGATGTCCCT AATCCTTCTC CAATACTAGG TTGTAATAGT ATACATGGCA AGGCTAGCTT  12060
TTTATGTCAG CTACTGGGAT TCAAACTCAG GTCTGGACAG CTGTTATTGT CAGCTGAGCC  12120
TTATCTGCTG TCTTTGTCAT TATCAGCTGG GTTTAAAAAG TATCCTTGAT CCTATTCTCA  12180
CCGTTCCCCA AACCCAAACA TTCCTGGGCA CCAGGGTTCC AAAGCATTCA GTGTGGAACC  12240
AAAGTTTCAG CTTCCTTGCC TTTGACCAAA GCAGTCTTGT GCTTCACAAC TGTCATAACT  12300
GTTGTCAAGG GCAACAAAGC CTCAGGGAGC AGCCAGATGA CCTCACTCCG TTTTGGCCA   12360
GAGACACAAA CTTTGCACTT GATCTTGTTT GTGCTTTTAA GCCCCGTTTT AGATGAGGTT  12420
CCTGGAAAAG CTAATCTCCA CGTCTTTTCA TTTTTCTGTT GAACCTTTCG TGATGCTTTC  12480
TAACTTAATT GCAATTTAAA AAGAGGCAGC TTGCTGTCCA GGAGGAATGA CACAAACACT  12540
AGGCCTCTGA GTGACTAAAG ACCATTTGAA ATGGGTCGTC ATCTATTACA GAAAATGTAA  12600
AATATACTTT ACACTTCTTA ACTATGTGCC TAAAGTATGT TTTATTTTGT TTTCCTCTAA  12660
AAAAAGAATT ATTTATTTTA CGTATTTGAG TACACTGTAG CTGACTTCAG ATCCACCAGA  12720
AGAGGGCCTT AGATTCCATT ACAGATGGTT GTGAGCTACC GTGTGATGGG AATTGAACTC  12780
AGGACCTCTG GAAAAGCAGT CAGTGCTCTT AACCACTGAG CCATCTTTCC GGCCTTTATT  12840
TTCCTTTTTT TAAAAAAAAA ATAAATGAAA AATTAACTTT TATTTCATGG GTGTATATAT  12900
GTATGGGCTC AAACATGATA TATGTGCATG GGCTCACACA TGCAGTGGTG CATGTATAAA  12960
AGTCAGAGAC AACTTGCAGA AGATGGTTTG CTCTTTTCAT CATATGGGCC CTGAGGATTA  13020
AACTCAAGTC ATCAGTTTTT GTGCCAACCC CCTTTACTCC CCGAGCCTTC TCTCAACAGC  13080
TCCTCACTTT ACCTTTTTAT TTAAAAAACA AACAAACAAA CAAACACCAA CCCAGCCTCC  13140
CACACAACAA CGAAAAGATC TCATGTAGCC CCAGGGTGGC TTTGAACTCC CCATATAGCT  13200
TAGGATGACT TTGAATTCCT AATGTTCTTG CCTCTACCTC CTAGTTACTA TGCCTGGCTT  13260
CTTACCATAG AATTTAAGAA ATTATCTAAG GTAAAGTGGT GTTATGTGCT TATAAGCCAG  13320
```

FIG.8E

```
GCACTCAGGA AGAAGCTAAG GCATGATGAT TGTGAGTTTG AAGCCAACCC AGGTTACAGA    13380
GGATCTCATC AAGAAATCAA CATTCAATTT TCAATTATTT CTTAAATTTT TTGAGGTTGG    13440
GCTGGAGGGG TTGGTTAAGA GCACTGGTTG GTCTTCCAGA GGACATGAGT TTGATTCCCT    13500
GTACCCCACA TGGTGGCTCA CAACCATCTG TAATTTTAAT TCTAGGGATC TAACGCCCTC    13560
TTCAAGCCTT CTCAGGCAGG TGCATAAGTA CACAGTCATA CATGCACAGA AAACACATAA    13620
ACATAAAATA AATAAATTAA AATTTTGAAA GTTTTTTTTG GGTGGAAGGT ACTTTTAAGT    13680
AACATTCTAT GTTATGGAAC AAGTGCATTC AATTTTACTA AGTTTTTAAT TTTAGCTTTT    13740
TGTTTGTTTG TTTTCTGTTT GGAACAAGGT CTTGTGTATC CCAAGCATCC TCAAAGTTGT    13800
TGTGTAGCGA AGGATGACCT TGAATTTTTT TATACTACTG CCTTCTTGAG GGCAAGCATT    13860
TTAATATAGG CAAAATAAAC TTTAAACTTT GTTGCTGTG CAGGTATATA TGGTGTGCAA    13920
GTGTATCTGT GTGTGTGTGT GTGTGTGTGT GTGTGTGTGT GTGTGAGA GAGAGAGAGA    13980
GAGAGAGAGA GAGAGAGAGA GAGAGAGAGA GATTAGAGAA TAACTTGTGG AAGTTCTCTC    14040
CTTCTACCCT GTGGGTCCCA GGGTAAACTC GGGTTATAAG GCTTTGCACC CTTTTTCCCA    14100
CTGAGAACTT CTTGCTGGCC TCACTCCCTA TTTTATTTTA TTGGTGGCAG TACTATTGCT    14160
TTTGAATCCC ATCTGAAGCT TGTTTTTGTT GTTTGGTTTT TAAGGCAGTC TTAACTGTGA    14220
CCTAAGCTGG TTTAAAACTC ACAGGAATTA TCCACCTCCA CCTCCCAAGT GTTGGGGTTA    14280
CAGATGTGAG CCCCAAGCCT GAGTGCTTCT GAAAGCTGCT TTTTTTTATT TCAAAACTAT    14340
CTTTTCTCTG TGTGTAGGTC TGATTAGTTG TGGGGTTAGG TGGTGTCAGC ATGATCCATC    14400
ACTCTCCAGC TATTATTCTT AAAATGAAGG GTCTGGGGGC TGGGGATTTA GCTCAGTGGT    14460
AGAGCGCTTA CCTAGGAAGC GCAAGGCCCT GGGTTCGGTC CCCAGCTCCG AAAAAAAGAA    14520
CCAAAAAAAA AAAAAATGAA GGGTCTGGTG GCTGAGGAAA AAGCTCAGTT GCAAAAAAAC    14580
ATGAAAACCT GATTCAATCT GTAAAGCCCA CATAAAAGCC AGGCATGGCG GCATGCACCT    14640
ATAACCCCAG CACTGGGGAA ACAGAACAGG AGAATACCAA GAACTTGCTG GTCAGTCAGT    14700
CTAGTTTAAT TGGTGAGCTC CAAGCTCAGT GAGACCCTGT CTCAAAAATA AATGGAGATG    14760
ATCTGTCATC AAGACCTGGC CTCCATACAT ATATGCACAC ATGTTACTCC CTCACATGAA    14820
ACATATTTAT AAACAAACAT ATGCACACAC TTGTGCATAC ATGAACAGAT ATCTATATTG    14880
GCATACACAT TAAAACACAC ACACACATAT ATATATACAA AAGTGTGTAC AAACATAGGC    14940
ATAGTATACA ACCATGCATA AATGCACAGT CACACATATG AATGCATTCA TATTCACACA    15000
TGGACACATG AACACATACA TATATGCTAT ATCTTATATT ACACTCCATT ACTATCCCCC    15060
AGTCCAGGTT TCAAATATTT ACAAACAGAA AAGCGGGCTA CTACCTGTAC TTTTTCCCAA    15120
TTGCCTTTGA ACAGCGATCT CTCGACACCT GATCCCCGCA GTGCTCCCTG CGGCAGAGCT    15180
TCATCCGGAA ACAACCCCCA TGCACTCTAT TGATTTTAAT ACTGGGGATT ACCTGGAGCC    15240
TTGTAAAGCT AAACACATTG TCTACTGCTA AATACTTCAT TCTTTGCCCC TTTCCCATGG    15300
GGCGTTTTCA ATCCAGTTAT TTTTAGTGTG TTCTTAGATT TAAGCATCCA CTAGTACAGA    15360
TTCAAGGATA TTTTTATTAT CCCCCAAATA ACAGTATTTG TTAGGTGTAA CCTTGTAGTT    15420
TTTCCCCAGC GGCTAATTTA AATTGCTTTC ATGAATAGCC TATTCTGGAA AAGTAATTTT    15480
TTTTTTTTTT TTTTTTTTTG GGTTCTTTTT TTCGGAGCTG GGGACCGAAC CCAGGGCCTT    15540
GCGCTTCCTA GGTAAGCGCT CTACCACTGA GCTAAATCCC CAGCCCCAAT TCTGGACATT    15600
TCTTATAAAT GTCACTATGC TGTATGTGTT CTTTCAGCAT TGCAACACTT TGGTTCCTTT    15660
TTATGGCTCA ATACTGGTCT ACTTATGGAT CTACCACACT ATCTATCCAT TCATCTCAAC    15720
ATAGTCATGG GTGGTATTTC TACTTTGGGG CTATTATAAG CTTGCTAGGA GTATTTATGA    15780
CCACATCTTT AGATGCACTG ATGCATTCAT TTATCCTAAG AACAGATCCT GGATCATATG    15840
GTGGTTCTGT GTTCAAACAT CAGAGGCACC ACCATTTATT TTATAATAGG CATTTAAGAT    15900
TTGGGTATCT TCTAACTGGG TGGTGGTGGT ACATGCCTGT AGTCCCAGCT CCTGGGAGGC    15960
AGAGGCAAGT AGATCCGAAT TCTCGCCCTA TAGTGAGTCG TATTAGTCGA C             16011
```

FIG.8F      +11,795 (1st intron)

IDENTIFICATION OF A SMOOTH MUSCLE CELL (SMC) SPECIFIC SMOOTH MUSCLE HEAVY CHAIN (SM-MHC) PROMOTER/ENHANCER

This application claims the benefit under 35 U.S.C. § 119(e) of co-pending provisional Application No. 60/071,300, filed on Jan. 16, 1998, which is hereby incorporated by reference in its entirety.

1. INTRODUCTION

The present invention generally relates to promoters, enhancers and other regulatory elements of smooth muscle cells ("SMC"). The invention more particularly relates to methods for the targeted knockout, or over-expression, of genes of interest within smooth muscle cells. The invention further relates to methods of conferring smooth muscle cell specific gene expression in vivo.

2. BACKGROUND OF THE INVENTION

Smooth muscle cells, often termed the most primitive type of muscle cell because they most resemble non-muscle cells, are called "smooth" because they contain no striations, unlike skeletal and cardiac muscle cells. Smooth muscle cells aggregate to form smooth muscle which constitutes the contractile portion of the stomach, intestine and uterus, the walls of arteries, the ducts of secretory glands and many other regions in which slow and sustained contractions are needed.

Abnormal gene expression in SMC plays a major role in numerous diseases including, but not limited to, atherosclerosis, hypertension, stroke, asthma and multiple gastrointestinal, urogenitcl and reproductive disorders. These diseases are the leading causes of morbidity and mortality in Western Societies, and account for billions of dollars in health care costs in the United States alone each year.

In recent years, the understanding of muscle differentiation has been enhanced greatly with the identification of several key cis-elements and trans-factors that regulate expression of muscle-specific genes. Firulli A. B. et al., 1997, *Trends in Genetics,* 13:364–369; Sartorelli V. et al., 1993, *Circ. Res.,* 72:925–931. However, the elucidation of transcriptional pathways that govern muscle differentiation has been restricted primarily to skeletal and cardiac muscle. Currently, no transcription factors have yet been identified that direct smooth muscle-specific gene expression, or SMC myogenesis. Owens G. K., 1995, *Physiol. Rev.,* 75:487–517. Unlike skeletal and cardiac myocytes, SMC do not undergo terminal differentiation. Furthermore, they exhibit a high degree of phenotypic plasticity, both in culture and in vivo. Owens G. K., 1995, *Physiol. Rev.,* 75:487–517; Schwartz S. M. et al., 1990, *Physiol. Rev.,* 70:1177–1209. Phenotypic plasticity is particularly striking when SMC located in the media of normal vessels are compared to SMC located in intimal lesions resulting from vascular injury or artherosclerotic disease. Schwartz S. M., 1990, *Physiol. Rev.,* 70:1177–1209; Ross R., 1993, *Nature,* 362:801–809; Kocher O. et al., 1991, *Lab. Invest.,* 65:459–470; Kocher O. et al., 1986, *Hum. Pathol.,* 17:875–880. Major modifications include decreased expression of smooth muscle isoforms of contractile proteins, altered growth regulatory properties, increased matrix production, abnormal lipid metabolism and decreased contractility. Owens G. K., 1995, *Physiol. Rev.,* 75:487–517. The process by which SMC undergo such changes is referred to as "phenotypic modulation". Chamley-Campbell J. H. et al., 1981, *Atherosclerosis,* 40:347–357. Importantly, these alterations in expression patterns of SMC protein cannot simply be viewed as a consequence of vascular disease, but rather are likely to contribute to progression of the disease.

A key to understanding SMC differentiation is to identify transcriptional mechanisms that control expression of genes that are selective or specific for differentiated SMC and that are required for its principal differentiated function, contraction. Currently, studies are ongoing in which the expression of the contractile proteins SM α-actin (Shimizu R. T. et al., 1995, *J. Biol. Chem.,* 270:7631–7643; Blank R. S. et al., 1992, *J. Biol. Chem.,* 267:984–989) and SM myosin heavy chain (SM-MHC)(White S. L. et al., 1996, *J. Biol. Chem.,* 271:15008–15017; Katoh Y. et al., 1994, *J. Biol. Chem.,* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851), as well as a variety of proteins implicated in control of contraction including SM22α (Li L. et al., 1996, *J. Cell. Biol.,* 132:849–859; Kim S. et al., 1997, *Mol. Cell. Biol.,* 17:2266–2278), $h_1$-calponin (Miano J. M. et al., 1996, *J. Biol. Chem.,* 271:7095–7103), h-caldesmon (Yano H. et al., 1994, *Biochem. Biophys. Res. Commun.,* 201:618–626), telokin (Herring B. P. et al., 1996, *Am. J. Physiol.,* 270:C1656–C1665) and desmin (Bolmont C. et al., 1990, *J. Submicrosc. Cytol. Pathol.,* 22: 117–122) are being examined. Of these gene products, only SM-MHC expression appears to be completely restricted to SMC lineages throughout development (Miano J. et al., 1994, *Circ. Res.,* 75:803–812), whereas all others show at least transient expression in non-SMC tissues (Owens G. K., 1995, *Physiol. Rev.,* 75:487–517). As such, it appears that the SM-MHC gene is unique with regard to its potential utility for identification of SMC-specific transcriptional regulatory pathways and mechanisms.

To date, four SM-MHC isoforms (SMC-1A, SMC-1B, SMC-2A and SMC-2B) have been identified (Nagai R. et al., 1989, *J. Biol. Chem.,* 264:9734–9737; White S. et al., 1993, *Am. J. Physiol.,* 264:C1252–C1258; Kelley C. A. et al., 1993, *J. Biol. Chem.,* 268:12848–12854), all of which are derived from alternative splicing of a single gene (Miano J. et al. 1994, *Circ. Res.,* 75:803–812; Babij P. et al., 1989, *J. Mol. Biol.,* 210:673–679). Alterations in expression of SM-MHC isoforms have been extensively documented in SMC that have undergone phenotypic modulation either when placed in culture (Rovner A. S., 1986, *J. Biol. Chem.,* 261:14740–14745; Kawamoto S. et al., 1987, *J. Biol. Chem.,* 262:7282–7288), or in vascular lesions of both humans and several animal models of vascular disease (Aikawa M. et al., 1997, *Circulation,* 96:82–90; Sartore S, et al., 1994, *J. Vasc. Res.,* 31:61–81). Thus, the SM-MHC gene represents an excellent candidate gene for delineating transcriptional pathways important for both normal development and diseased states.

Transcriptional regulation of the SM-MHC gene has been analyzed extensively in cultured SMC and several functional cis-elements have been identified. White S. L. et al., 1996, *J. Biol. Chem.,* 271:15008–15017; Katoh Y. et al., 1994, *J. Biol. Chem.,* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851. However, because differentiation of SMC is known to be dependent on many local environmental cues that cannot be completely reproduced in vitro, cultured SMC are known to be phenotypically modified as compared to their in vivo counterparts (Owens G. K., 1995, *Physiol. Rev.,* 75:487–517; Chamley-Campbell J. H. et al., 1981, *Atherosclerosis,* 40:347–357). As such, certain limitations may apply regarding the usefulness of cultured SMC in defining transcriptional programs that occur during normal SMC differentiation and maturation within the animal.

Prior to the instant invention, no genetic elements that are completely specific for SMC and which have been proven to confer smooth muscle specific gene expression in vivo in transgenic animals have been defined, isolated or identified. Furthermore, as discussed above, previously characterized smooth muscle cell gene promoters including those for SM 22α and SM α-actin show activity in both SMC and non-SMC, thus limiting their use for purposes requiring SMC-specific gene targeting.

The current invention provides the major advance of identifying molecular elements that confer SMC-specific transcription in vivo during normal development. More specifically, the instant invention utilizes transgenic mice to identify DNA sequences that are critical for SM-MHC expression. Thus, the instant invention provides, for the first time, the identification of sufficient regions of the SM-MHC gene to direct SMC-specific expression both in vitro in cultured SMC and in vivo in transgenic mice. Therefore, the instant invention can be used, for example, for the targeted knockout, or over-expression, of genes of interest within smooth muscle cells. Potential applications for the instant invention include, for example, the treatment or possible cure of the many diseases involving smooth muscles, including, but not limited to, coronary artery disease, asthma and hypertension.

3. SUMMARY OF THE INVENTION

The present invention generally relates to promoters, enhancers and other regulatory elements of genes. More particularly, the invention is directed to regulatory elements that confer SMC-specific gene expression both in vitro and in vivo.

One aspect of the invention relates to the use of SM-MHC promoters and other regulatory elements to control the expression of protein and RNA products in SMC. SM-MHC promoters and other regulatory elements have a variety of uses including, but not limited to, expressing heterologous genes in SMC tissues, such as the contractile portion of the stomach, intestine and uterus, the walls of arteries, the ducts of secretory glands and many other regions in which slow and sustained contractions are needed.

Another aspect of the invention relates to the use of SM-MHC promoters and other regulatory elements for genetic engineering as a means to investigate SMC physiology and pathophysiology. For example, a specific gene that is believed to be important for a specific disease within SMC could be knocked out with the confounding influences of knocking out that gene in other cell types and tissues. This could be accomplished by methods well known to those of skill in the art. For example, an antisense polynucleotide could be expressed under the control of an SM-MHC that would inhibit a target gene of interest, or an inhibitor could be expressed that would specifically inhibit a particular protein.

In an alternative embodiment of the invention, the SM-MHC promoter/enhancer is used to carry out targeted knockout of genes of interest. For example, a number of tetracycline-cre-recombinase based mouse systems can be used to obtain SMC targeting of cre-recombinase dependent genes (i.e. "floxed" genes containing lox p cre recombinase recognition sites) of interest. Further, one could examine how selective (SMC-specific) knockout of an SMC gene of interest affects development of coronary artery disease without the confounding limitations of conventional knockouts with respect to deducing the primary site of action, activation of compensatory pathways, etc. The feasibility of these sorts of approaches has been shown in other, non-SMC, tissue types (see, Mayford et al., *Science* 274:1678, 1996). However, the invention described herein discloses, for the first time, such studies in SMC tissues. For example, the SM-MHC of the instant invention can be used in combination with the tetracycline-cre-recombinase based mouse systems to effectuate targeted knockouts of various genes which are implicated in the control of SMC differentiation within SMC tissues. (Hautmann et al. *Circ. Res.* 81:600, 1997; Blank et al., *Circ. Res.* 76:742, 1995; Madsen et al, *J. Biol. Chem.* 272:6332,1997, each of which is incorporated by reference in its entirety). Examples of such genes include genes which encode for serum response factor, the homeodomain protein MHox and the retinoic acid α-receptor. It is of interest that conventional (non-targeted) knockout of these genes results in embryonic lethality, thus precluding the utility of studying involvement of these genes in control of SMC differentiation in diseases such as atherosclerosis, hypertension, asthma, etc.

Figure 6:
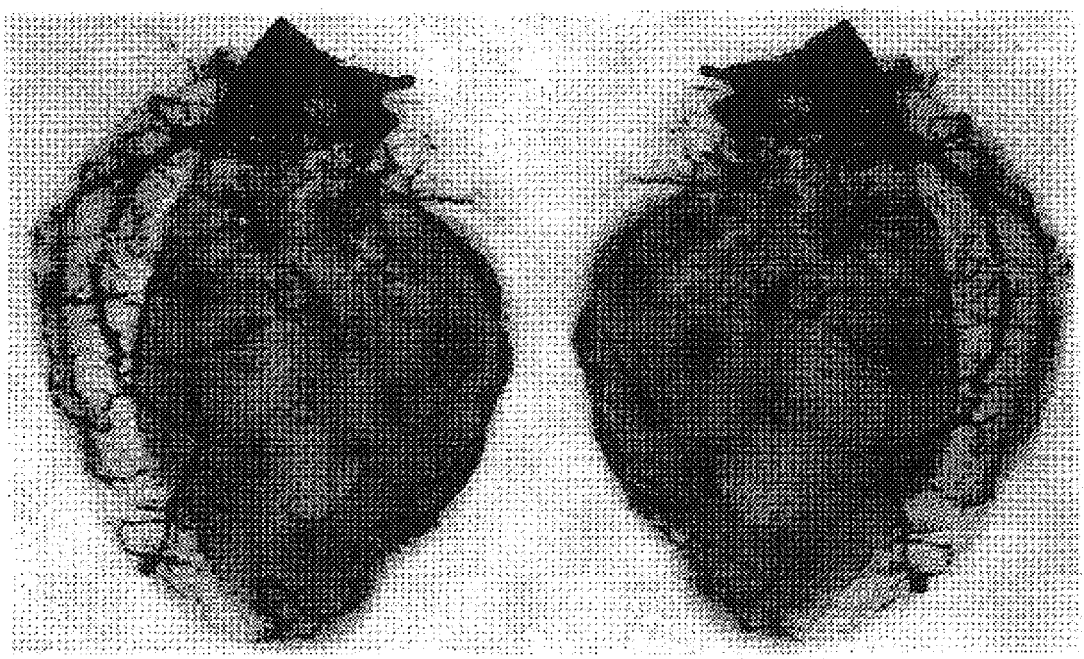

A major biomedical application of the invention would be to use the SM-MHC regulatory region to over-express a gene of interest within SMC. For example, an inhibitor of a pathologic process within an SMC tissue may be over-expressed in order to generate a high, local concentration of the factor that might be needed for a therapeutic effect. Since expression of the gene would be SMC-specific, undesired side effects on other tissues that often result when conventional systemic administration of therapeutic agents are utilized would be avoided. For example, a gene for an SMC relaxant could be over-expressed within bronchiolar SMC as a therapy for asthma, or an inhibitor of SMC growth could be over-expressed to prevent development of atherosclerosis or post-angioplasty restinosis. As shown in FIG. 6, the SM-MHC transgene of the instant invention was specifically expressed at high levels within all coronary arteries and arterioles within the heart of an adult mouse, thus demonstrating the efficacy of the SM-MHC promoter/enhancer for gene therapy for coronary artery disease.

The present invention is based, in part, on the identification of an SM-MHC promoter-intronic DNA fragment that directs smooth muscle-specific expression in transgenic mice. Transgenic mice harboring an SM-MHC-lacZ reporter construct containing approximately 16 kb of the SM-MHC genomic region from about −4.2 kb to about +11.7 kg (within the first intron) expressed the lacZ transgene in all smooth muscle tissue types. The inclusion of intronic sequence was required for transgene expression since 4.2 kb of the 5' flanking region alone was not sufficient for expression.

Furthermore, in the adult mouse, transgene expression was observed in both arterial and venous smooth muscle, airway smooth muscle of the trachea and bronchi and in the smooth muscle layers of all abdominal organs, including the stomach, intestine, ureters and bladder. In addition, of particular significance, the transgene was expressed at high levels throughout the coronary circulation. (See, FIG. 6). During development, transgene expression was first detected in airway SMC at embryonic day 12.5 and in vascular and visceral SMC tissues by embryonic day 14.5.

Thus, the present invention discloses for the first time, a promoter/enhancer region of SM-MHC that confers complete SMC specificity in vivo, thus providing a system with which to define SMC-specific transcriptional regulatory elements, and to design vectors for SMC-specific gene targeting.

4. BRIEF DESCRIPTION OF THE FIGURES

FIGS. 1A–H. Gross examination of SM-MHC 4.2-Intron-lacZ expression in various smooth muscle containing tissues. Transgenic mice (5–6 week-old) were perfusion fixed with a 2% formaldehyde/0.2% paraformaldehyde solution and various smooth muscle containing tissues were harvested and stained overnight at room temperature for β-galactosidase activity using 5-bromo-chloro-3-indolyl-β-D galactopyranoside (X-Gal) as the substrate. Panel A: Thoracic organs removed en bloc showing specific staining of SM-containing tissue (founder line 2282). Panel B: Anterior view of the heart (atria removed) showing staining of the major branches of the coronary arterial tree (founder line 2282). Panel C: View of thoracic aorta with attached intercostal arteries showing staining of a majority of the SMC (founder line 2820). Panel D: Cross section of the heart showing staining of cross sections of small coronary vessels throughout the intraventricular septum and right and left ventricles (founder line 2820). Panel E: Mesentery removed en bloc showing specific staining of large and small mesenteric arteries and veins (founder line 2642). Panel F: Section of jejunum demonstrating staining of a majority of gut SMC (founder line 2820). Panel G: View of genito-urinary tract showing intense staining of the ureter and bladder (founder line 2282). Panel H: View of esophagus and stomach showing staining of a majority of SMC in the stomach with little or no staining of the esophagus (founder line 2642).

FIGS. 2A–F. Histological analysis of SM-MHC 4.2-Intron-lacZ expression in various smooth muscle containing tissues. Transgenic mice (5–6 week-old) were perfusion fixed with a 2% formaldehyde/0.2% paraformaldehyde solution and various smooth muscle containing tissues were harvested and stained overnight at room temperature for β-galactosidase activity using 5-bromo-chloro-3-indolyl-β-D-galactopyranoside (X-Gal) as the substrate. After staining with X-Gal overnight, tissues were processed for paraffin embedding, sectioned at 6 μm, and sections counterstained with hematoxylin/eosin. Panel A: Cross section of the trachea showing complete staining of all smooth muscle cells (large arrowhead). Panel B: Cross section of the thoracic aorta showing heterogeneous staining of smooth muscle. The large arrowhead indicates a VSMC stained positively for β-Gal activity while the small arrowhead indicates an adjacent negatively stained SMC. Panel C: Representative cross section of the left ventricle showing various small coronary arteries, arterioles and veins. Large arrowheads point to positively stained vessels or portions of vessels while small arrowheads denote unstained vessels. Panel D: Cross section of small intestine showing a mosaic of positively labeled SMC (large arrowhead) and unstained SMC (small arrowhead). Panel E: Cross section of a second order mesenteric arteriole showing staining of a majority (large arrowhead), but not all (small arrowhead), of the vessel. Panel F: Cross section of parenchymal blood vessels of the small intestine which shows a partially positive vein, a positively labeled arteriole (large arrowhead) and an adjacent unstained arteriole (small arrowhead).

Figure 3:
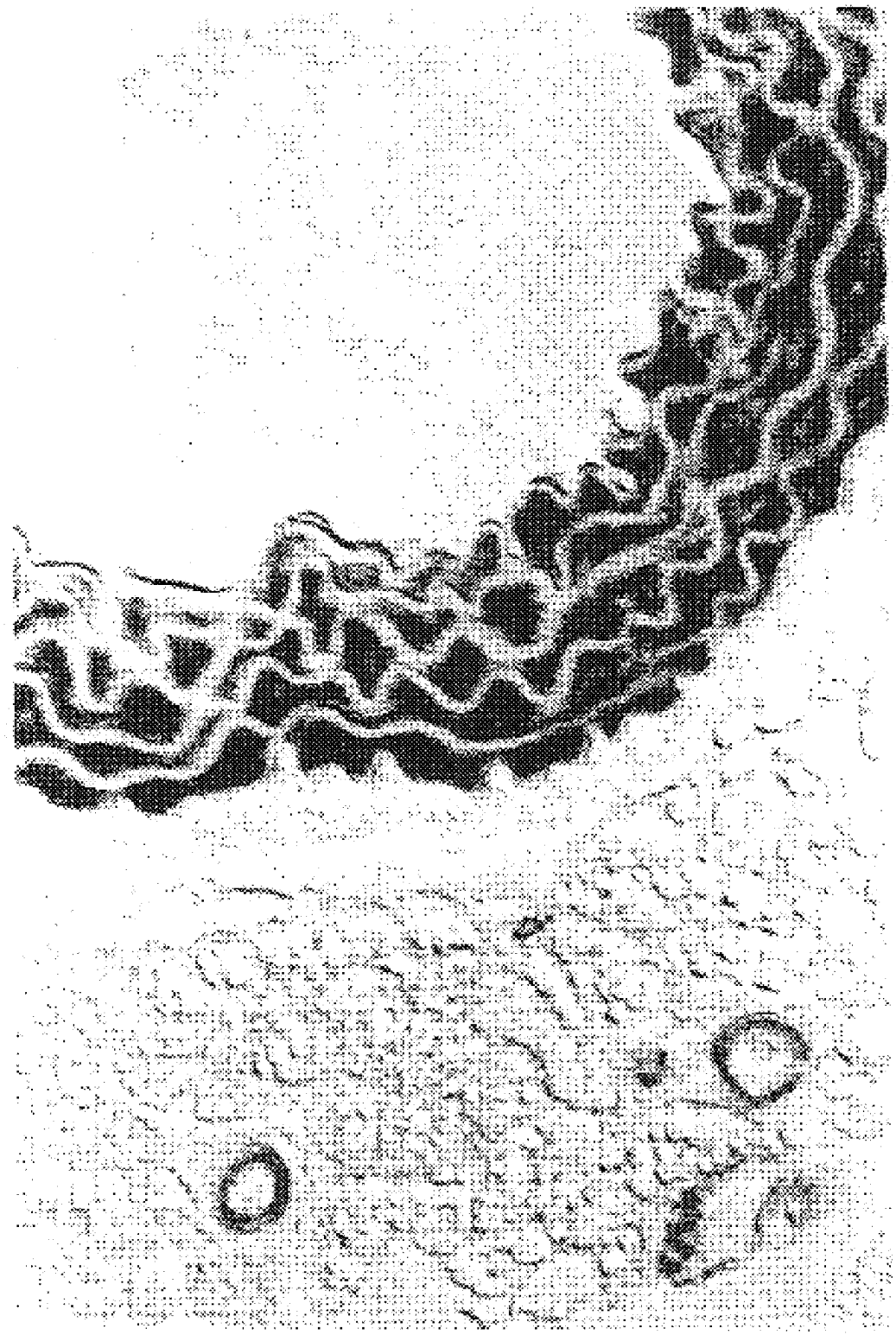
Figure 4A:
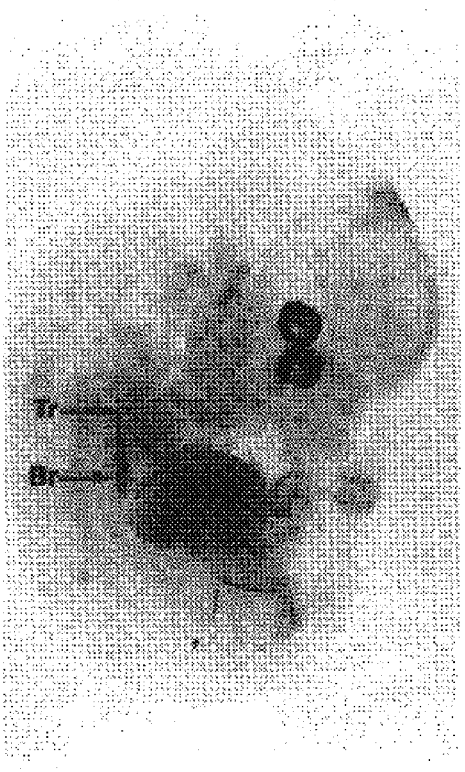
Figure 4B:
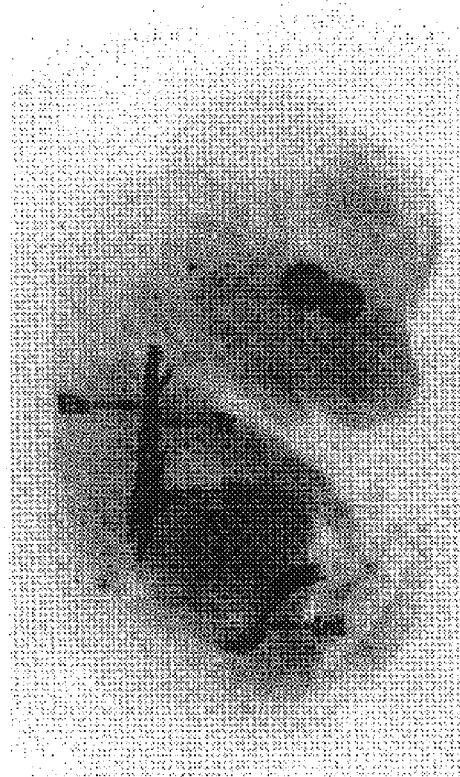
Figure 4C:
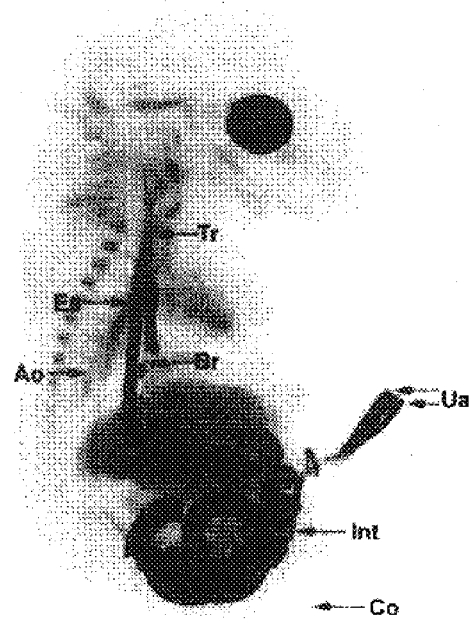
Figure 4D:
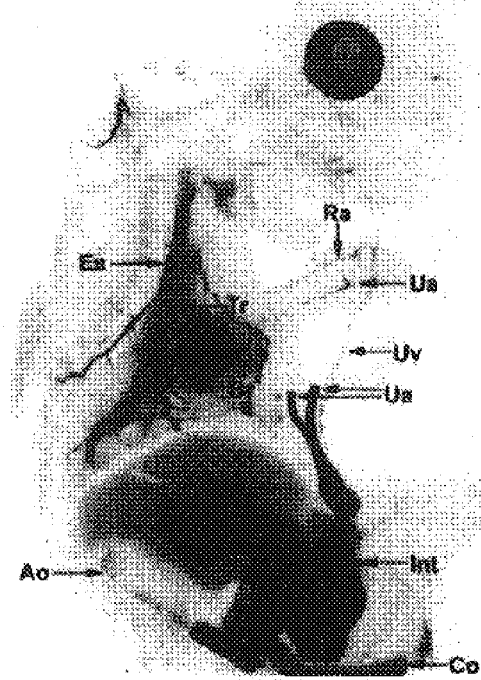

FIG. 3. Immunostaining of adult thoracic aorta with a rabbit anti-chicken gizzard SM-MHC polyclonal antibody. The descending thoracic aorta was removed from a 5–6 week-old transgenic mouse and fixed overnight in methacarn. The tissue was then dehydrated, embedded in paraffin and sectioned at 6 μm. Sections were incubated with a rabbit anti-chicken gizzard smooth muscle myosin polyclonal antibody, and detection performed using DAB as the chromagen. This antibody showed specific reactivity with both SM1 and SM2 isoforms of SM-MHC as well as with non-muscle myosin heavy chain B (or SMEMB) in Western analyses (Raines and Owens, unpublished observations). However, consistent with previous findings in other species (Rovner A. S. et al., (1986), *J. Biol. Chem.,* 261: 14740–14745; Rovner A. S. et al., (1986), *Am. J. Physiol.,* 250:c861–c870; Phillips C. L. et al., (1995), *Res. & Cell. Motility,* 16:379–389), SMEMB was undetected within adult mouse aortic medial SMC by Western analyses, such that the staining observed primarily reflects reactivity with SM-MHC isoforms. Sections were counterstained with hematoxylin to facilitate visualization of individual cell nuclei.

FIGS. 4A–D. Expression of SM-MHC 4.2-Intron-lacZ throughout development. Embryos were harvested at various time points (10.5–16.5 days p.c.), fixed with a 2% formaldehyde/0.2% paraformaldehyde solution and stained overnight at room temperature for β-galactosidase activity using 5-bromo-chloro-3-indolyl-β-D galactopyranoside (X-Gal) as the substrate. Embryos were then cleared in benzyl benzoate:benzyl alcohol (2:1). Panel A: 10.5 days p.c. Panel B: 12.5 days p.c. Panel C: 14.5 days p.c. Panel D: 16.5 days p.c.

Figure 5A:
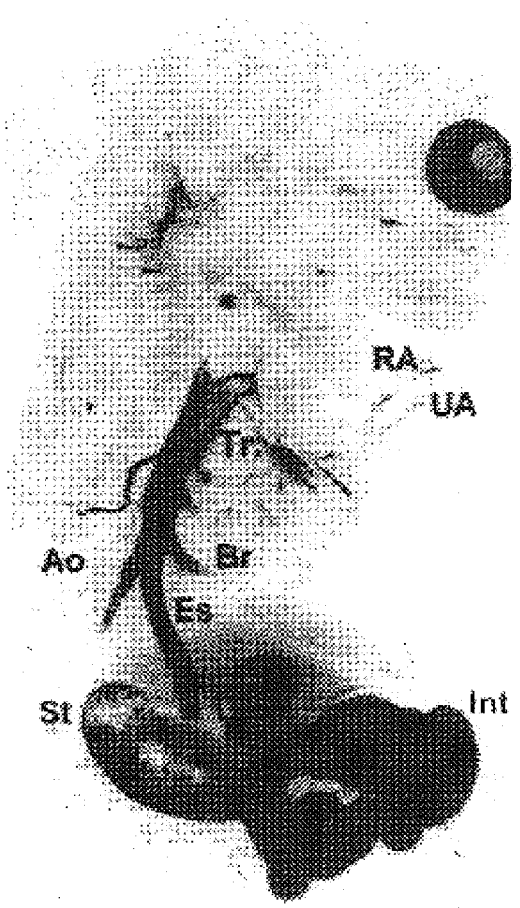
Figure 5B:
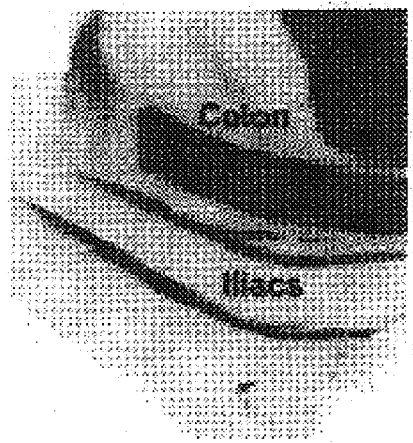
Figure 5C:
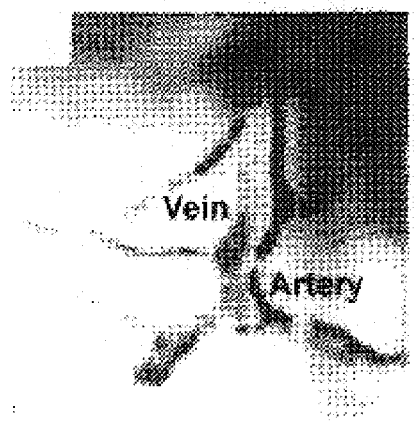

FIG. 5. Expression of SM-MHC 4.2-Intron-lacZ at 19.5 days p.c. Embryos were harvested at 19.5 days p.c. fixed with a 2% formaldehyde/0.2% paraformaldehyde solution and stained overnight at room temperature for β-galactosidase activity using 5-bromo-chloro-3-indoyl-β-D-galactopyranoside (X-Gal) as the substrate. Embryos were then cleared in benzyl benzoate:benzyl alcohol (2:1). Panel A: Saggital section of 19.5 day embryo. Panel B: Closeup of thoracic cavity. Panel C: Iliac artery and vein.

FIG. 6. Expression of the SM-MHC 4.2-Intron-lacZ transgene in the coronary circulation of the heart of an adult mouse. High levels of SMC-specific expression are present in all major coronary arteries and arterioles.

Figure 7:
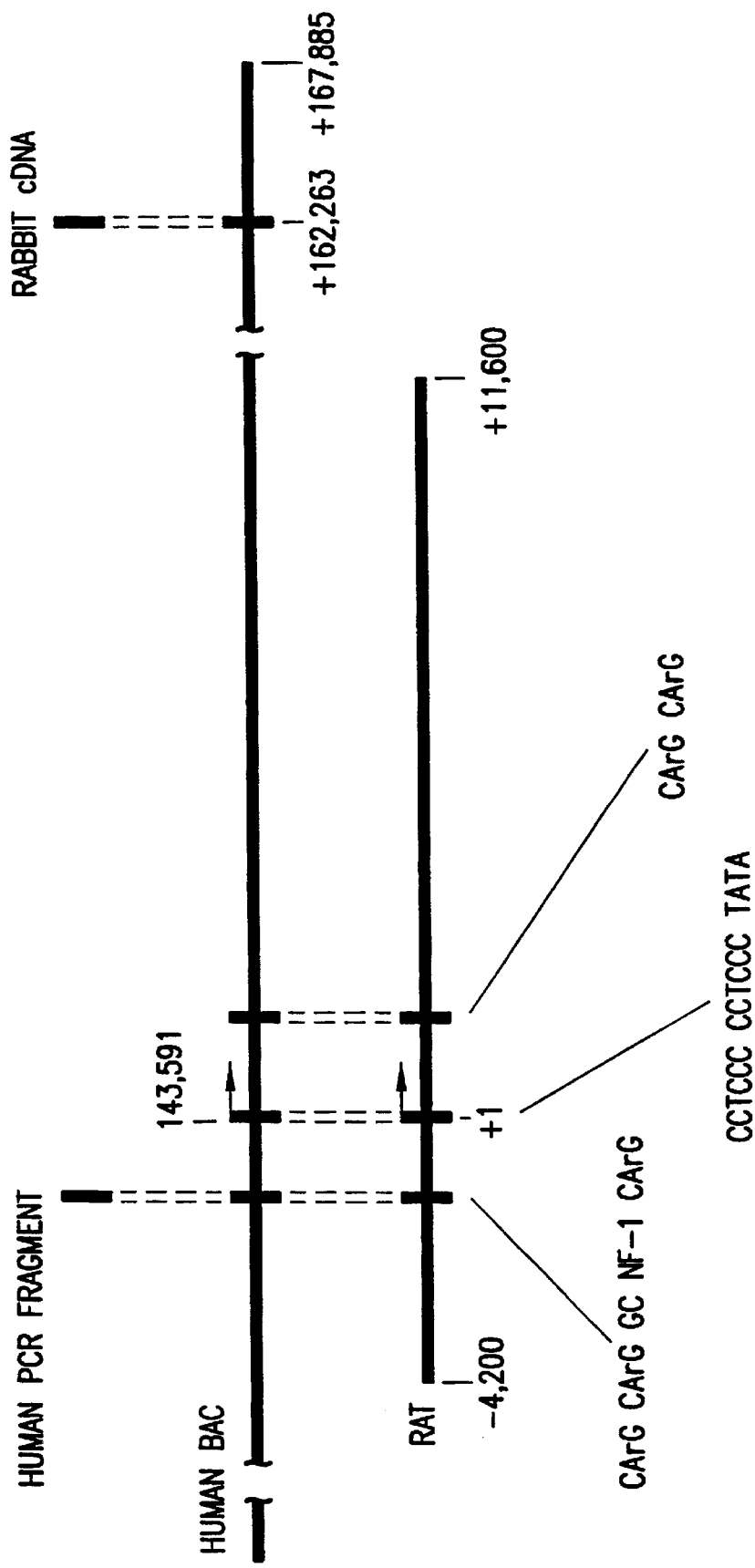

FIG. 7. Schematic representation of the rat SM-MHC 4.2-Intron-lacZ clone and a comparable region of the human SM-MHC gene. As indicated, there is conversation of key regulatory elements including the CArG boxes, the GC repressor and an NF-1 site.

FIGS. 8A–F. Nucleotide sequence of the entire rat SM-MHC 4.2-Intron region employed in transgenic studies (SEQ ID NO:3). As noted on the Figure, the nucleotide position 1 corresponds with position −4,216 base pairs relative to the SM-MHC transcription start site, which is shown in FIG. 8B.

Figure 9:
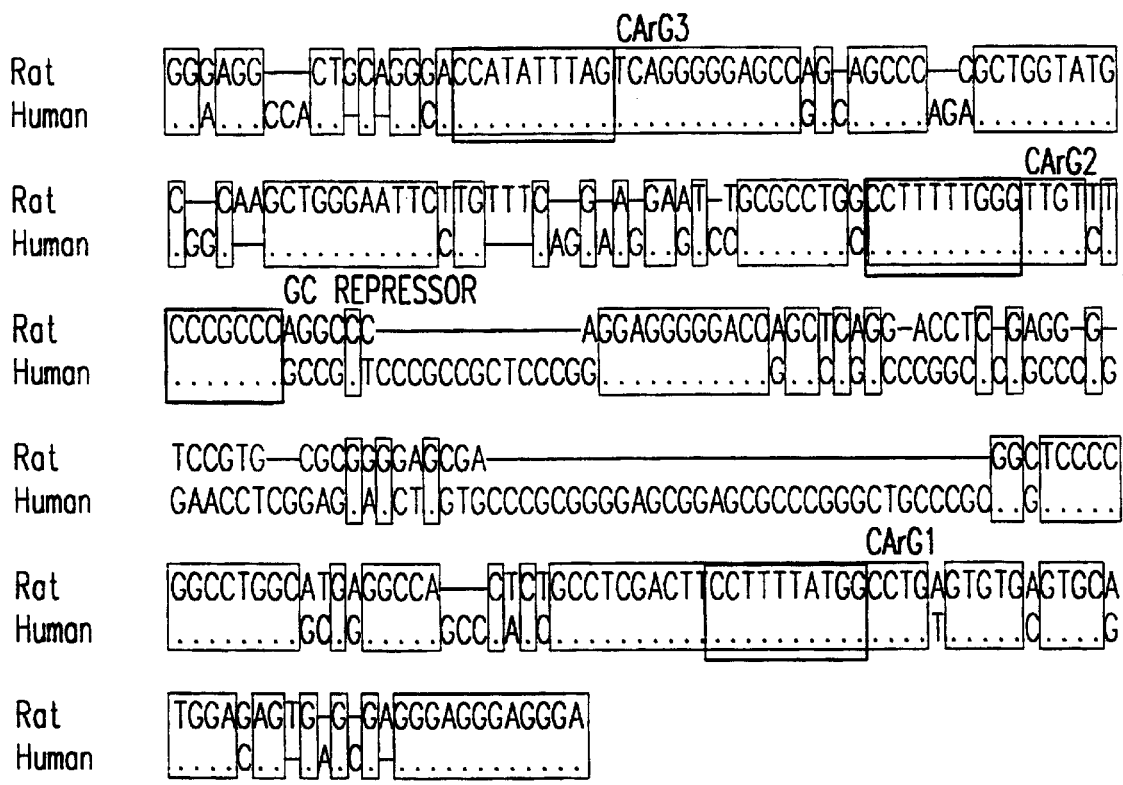

FIG. 9. Nucleotide sequence comparison of the rate (SEQ ID NO:1) and human (SEQ ID NO:2) SM-MHC promoter/enhancer sequence within the 5' promoter region. As indicated, there is complete sequence homology between the rat and human genes in the key regulatory regions identified thus far (e.g. 5' CArG 1, 2 and 3; the G/C repressor, etc., as indicated). The identity of these elements in the rabbit and mouse genes have been shown previously. See, Madsen et al., 1997, *J. Biol. Chem.,* 272:6332.

5. DETAILED DESCRIPTION OF THE INVENTION

The present invention relates to promoters, enhancers and other regulatory elements of SMC. The SMC promoters/enhancers of the instant invention may be used in expression constructs to express desired heterologous gene products specifically within SMC, such as, for example, cells which form the contractile portion of the stomach, intestine and uterus, the walls of arteries, the ducts of secretory glands and many other regions in which slow and sustained contractions are needed. Furthermore, transgenic animals can be produced in which specific genes are either knocked-out or over-expressed within SMC. These transgenic animals can be used as animal models of human disease and can be used for testing the efficacy of drugs in disorders involving SMC, as well as for identifying the underlying causes of these diseases and for developing novel therapies.

The SM-MHC promoters/enhancers are used in accordance with the invention in gene replacement therapy. To effectuate such gene therapy, one or more copies of a normal target gene, or a portion of the gene that directs the production of a normal target gene protein with target gene function, may be operatively fused to the SM-MHC and inserted into cells using vectors which include, but are not limited to, adenovirus, adeno-associated virus and retrovirus vectors. In addition, other compounds which allow for the introduction of DNA into cells, such as liposomes, for example, may be used during transformation and transfection of target cells. The vectors or liposomes carrying the SM-MHC-therapeutic gene constructs can be directly administered to patients. Alternatively, these constructs can be introduced into cells ex vivo.

Once the cells, preferably autologous SMC, containing normal target genes that are operatively associated with the SM-MHC promoter/enhancer are obtained, they may then be introduced or reintroduced into the patient at positions which allow for the amelioration of SMC-related disease, since the SM-MHC promoter/enhancer of the instant invention confers expression only in SMC. Such cell replacement techniques may be preferred, for example, when the target gene product is localized within SMC. Examples of techniques for introducing cells into a patient are well known to those of skill in the art. See, e.g., March, 1996, *Semin. Interv. Cardiol.*, 3:215–223; Stephan and Nabel, 1997, *Fundam. Clin. Pharmacol.*, 11:97–110.

A specific example would be to use the SM-MHC promoter/enhancer of the instant invention to target overexpression of nitric oxide (NO) synthase to SMC. NO synthase is an enzyme that produces nitric oxide, a potent and efficacious SMC relaxant and growth inhibitor. Ignarro, 1989, *Circ. Res.*, 65:191. Over-expression of NO could be used, for example, as a means to cure hypertension. Although a general limitation of gene therapy methods has been the inability to get the therapeutic gene into a large fraction of the target cells of interest, a variety of methods have been developed to accomplish this in at least some SMC tissues including blood vessels. Ohno et al., 1994, *Science*, 268:781. Furthermore, using the SM-MHC promoter/enhancer in operative association with a target gene of interest, SMC-specific expression of the target gene will be achieved.

The vectors, liposomes or cells containing the SM-MHC-target gene constructs can be formulated for administration using techniques well known in the art. The identified compounds that inhibit target gene expression, synthesis and/or activity can be administered to a patient at therapeutically effective doses to treat or ameliorate SMC-related disease. A therapeutically effective dose refers to that amount of the compound sufficient to result in amelioration of symptoms of the disease.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscular) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

According to the present invention, SMC promoters/enhancers and functional portions thereof described herein refer to regions of the SM-MHC gene which are capable of promoting SMC-specified expression of an operably linked coding sequence in various SMC. The SMC promoter/enhancer described herein refers to the regulatory elements of the SM-MHC gene which confers cell-specific expression within SMC.

Methods which can be used for the synthesis, isolation, molecular cloning, characterization and manipulation of SMC promoter/enhancer sequences are well known to those skilled in the art. See, e.g., the techniques described in Sambrook et al., Molecular Cloning: A Laboratory Manual, 2nd. ed., Cloning Spring Harbor Laboratory, Cold Spring Harbor, N.Y. (1989).

SMC promoter/enhancer sequences or portions thereof described herein may be obtained from appropriate sources from cell lines or recombinant DNA constructs containing SMC promoter/enhancer sequences, and/or by chemical synthetic methods. SMC promoter/enhancer sequences can be obtained from genomic clones containing sequences 5' upstream of SMC coding sequences. Such 5' upstream clones may be obtained by screening genomic libraries. Standard methods that may used in such screening include, for example, the method set forth in Benton & Davis, 1997, *Science* 196:180 for bacteriophage libraries; and Grunstein & Hogness, 1975, *Proc. Nat. Acad. Sci. U.S.A.* 72:3961–3965 for plasmid libraries.

According to the present invention, an SMC promoter/enhancer is one that confers to an operatively associated polynucleotide, cell-specific expression within SMC, such as, for example, cells which form the contractile portion of the stomach, intestine and uterus, the walls of arteries, the ducts of secretory glands and many other regions in which slow and sustained contractions are needed. In a specific embodiment of the present invention, an approximately 16 kb promoter-intronic fragment (about −4216 to about +11, 795) of the rat SM-MHC gene was utilized to confer SMC-specific expression in vivo. FIGS. 8A–F.

In addition to the SMC promoter/enhancer elements discussed above, other SMC promoters/enhancers of the instant invention include homologous SMC promoter/enhancer elements which have similar functional activity. This includes SMC promoters/enhancers which direct SMC-specific expression in vivo and either hybridize to the rat SM-MHC promoter/enhancer under highly stringent conditions, e.g., hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), or that hybridize to the complement of the above-described promoter/enhancer under less stringent conditions, such as moderately stringent conditions, e.g., washing in 0.2×SSC/0.1% SDS at 42° C. (Ausubel et al., 1989, supra), or that hybridize to the complement of the above-described promoter/enhancer under low stringency conditions, e.g., washing in 2×SSC/0.1% SDS.

The present invention also encompasses assays for identifying compounds that modulate expression of SM-MHC. Specifically, the activity of the SM-MHC promoter/enhancer of the instant invention is determined by its ability to direct transcription of a polynucleotide sequence with which it is operatively associated. Such modulatory compounds are useful in enhancing or inhibiting the expression of genes transcribed by the SM-MHC in accordance with the invention, thus providing additional control and specificity over their expression. Compounds and other substances that modulate expression of the SM-MHC promoter/enhancer can be screened using in vitro cellular systems. After applying a compound or other substance to the test system, RNA can be extracted from the cells. The level of transcription of a specific target gene can be detected using, for example, standard RT-PCR amplification techniques and/or Northern analysis. Alternatively, the level of target protein production can be assayed by using antibodies that detect the target gene protein. Preferably, the SM-MHC can be fused to a reporter gene and the expression of the reporter gene can be assessed. Such reporter genes, for which assays are well known to those of skill in the art, include, but are not limited to lacZ, β-glucoronidase, enhanced green fluorescence protein, etc. See, e.g., Khodjakov et al., 1997, *Cell. Motil. Cytoskeleton*, 38:311–317. The level of expression is compared to a control cell sample which was not exposed to the substance. The activity of the compounds also can be assayed in vivo using transgenic animals according to the methods described, for example, in Examples 4–7, below.

Compounds that can be screened for modulation of expression of the target gene include, but are not limited to, small inorganic or organic molecules, peptides, such as peptide hormones analogs, steroid hormones, analogs of such hormones, and other proteins. Compounds that downregulate expression include, but are not limited to, oligonucleotides that are complementary to the 5'-end of the mRNA of the SM-MHC and inhibit transcription by forming triple helix structures, and ribozymes or antisense molecules which inhibit translation of the target gene mRNA. Techniques and strategies for designing such down-regulating test compounds are well known to those of skill in the art.

Local cis-regulatory elements within an SMC promoter/enhancer may also be used to effect SMC-specific expression in accordance with the invention. Such local cis-elements can be identified using methods of molecular genetic analysis well known in the art. For example, the location of cis-regulatory elements within a promoter/enhancer may be identified using methods such as DNase or chemical footprinting (e.g., Meier et al., 1991, *Plant Cell* 3:309–315) or gel retardation (e.g., Weissenborn & Larson, 1992, *J. Biol. Chem.* 267-6122–6131; Beato, 1989, *Cell* 56:335–344; Johnson et al., 1989, *Ann. Rev. Biochem.* 58:799–839). Additionally, resectioning experiments also may be employed to define the location of the cis-regulatory elements. For example, a promoter/enhancer-containing fragment may be resected from either the 5' or 3' end using restriction enzyme or exonuclease digests.

To determine the location of cis-regulatory elements within the sequence containing the promoter/enhancer, the 5' or 3' resected fragments, internal fragments to the promoter/enhancer containing sequence or promoter/enhancer fragments containing sequences identified by footprinting or gel retardation experiments may be fused to the 5' end of a truncated promoter, and the activity of the chimeric promoter/enhancer in transgenic animal examined. Useful truncated promoters to these ends comprise sequences starting at or about the transcription initiation site and extending to no more than 150 bp 5' upstream. These truncated promoters generally are inactive or are only minimally active. Examples of such truncated plant promoters may include, among others, a "minimal" CaMV 35S promoter whose 5' end terminates at position −46 bp with respect to the transcription initiation site (Skriver et al., *Proc. Natl. Acad. Sci. USA* 88:7726–7270); the truncated "−90 35S" promoter in the X-GUS-90 vector (Benfey & Chua, 1989, *Science* 244:174–181); a truncated "−101 nos" promoter derived from the nopaline synthase promoter (Aryan et al., 1991, *Mol. Gen. Genet.* 225:65–71); and the truncated maize Adh-1 promoter in pADcat 2 (Ellis et al., 1987, *EMBO J.* 6:11–16).

According to the present invention, a cis-regulatory element of an SMC promoter/enhancer is a sequence that confers to a truncated promoter tissue-specific expression in various SMC. It has previously been shown that multiple cis-elements contained within the first 4.2-kb of 5'-flanking sequence of the SM-MHC promoter are critical for expression in cultured SMC. (White S. L. et a., 1996, *J. Biol. Chem.,* 271:15008–15017; Katoh Y. et al., 1994, *J. Biol. Chem.,* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851). The fact that the p4.2-lacZ construct was found to be active in cultured SMC, but completely inactive in vivo, indicates that additional regulatory elements are necessary for expression within the in vivo context. Furthermore, the fact that the p4.2-Intron-lacZ construct containing approximately 16 kg of the rat SM-MHC genomic region from −4.2 kg to +11.7 kb was expressed in SMC-tissues within transgenic mice whereas the p4.2-lacZ construct was inactive, strongly suggests that the first 11.6 kb region of intron 1 contains enhancer elements required for expression in vivo but not in cultured SMC.

Differences in requirements for expression of the SM-MHC gene in cultured SMC versus in vivo in the mouse may be the result of the generalized phenotypic modulation of SMC that occurs in cell culture, or may reflect alterations in specific local environmental cues that differ between in vivo and in vitro conditions. Nevertheless, the present invention discloses a promoter/enhancer region within the SM-MHC gene which is sufficient to confer SMC-specific expression in vivo.

Although functional and structural heterogeneity of SMC both between and within different SMC tissues exists (Topouzis S. 1996, *Devel. Biol.,* 178:430–445; Giuriato L. et al., 1992, *J. Cell. Sci.,* 101:233–246; Frid M. G. et al., 1994, *Circ. Res.,* 75:669–681), this is not surprising given the plasticity of the SMC, and the fact that it must carry out very diverse functions at different development stages, and in response to injury or pathological stimuli. Majesky M. W. et al., 1990, *Toxicol. Pathol.,* 18:554–559. Despite the evidence for heterogeneity among SMC subpopulations, the underlying mechanisms responsible for phenotypic diversity are not well understood. Results disclosed in the instant invention reveal distinct patterns of transgene expression with respect to developmental stage and SMC tissue-type. For example, transgene expression was consistently not detected in certain blood vessels, including the pulmonary arteries and veins, at any developmental time point. In contrast, for the esophagus, a high level of transgene expression in the developing embryo was observed, but no expression was detected in adults, despite persistence of transgene expression in many other SMC tissues in adults (e.g. airways, intestine, coronary arteries, small arterioles and veins, etc.). Finally, heterogeneity was observed in expression between adjacent individual SMC within a given SMC tissue, as well as between blood vessels that lie in close proximity.

These apparent differences in transgene expression may simply reflect limitations of the methodology of detection. That is, heterogeneity may be a function of the sensitivity of the β-galactosidase assay rather than a reflection of distinct SMC sub-populations that express, or do not express, the transgene. Importantly, heterogeneity of expression of SM-MHC (Zanellato A. M. et al., 1990, *Dev. Biol.,* 141) and SM α-actin (Owens G. K. et al., 1986, *J. Biol. Chem.,* 261:13373–13380) within aortic SMC of newborn animals has been reported based on immunohistochemical studies, suggesting that there also may be differences in expression of these endogenous contractile protein genes at least during early post-natal development. However, heterogeneity of lacZ transgene expression was observed in adult SMC tissues in which 100% of the SMC showed detectable SM-MHC antibody staining (e.g. the aorta, FIG. 3). Clearly, the ability to detect SM-MHC gene expression is highly dependent upon whether one attempts to detect expression at the transcriptional versus the translational level, as well upon the sensitivity of the detection method employed. Indeed, such differences in detection methodology may explain the apparent discrepancies between the developmental time course of expression of the SM-MHC transgene disclosed in the instant invention as compared to detection of SM-MHC transcripts reported by Miano J. et al., 1994, *Circ. Res.,* 75:803–812.

The finding that the lacZ transgene was highly expressed in the esophagus during embryogenesis and was later undetectable in the adult may be the result of the rare phenomenon known as transdifferentiation. Using multiple skeletal and smooth muscle specific-markers (including SM-MHC), Patapoutian A. et al., 1995, Science, 270:1818–1822, demonstrated that esophageal muscle tissue changes, or "transdifferentiates", from a smooth muscle phenotype to a skeletal muscle phenotype during the late fetal to early postnatal stage in development. The fact that this transition in phenotype was closely mimicked by the esophageal expression pattern of the SM-MHC transgene supports the transdifferentiation data and further suggests that the p4.2-Intron-lacZ construct contained sufficient sequence for proper regulation in this tissue-type.

Thus, the present invention not only discloses a sufficient region of the SM-MHC gene to drive SMC specific expression in transgenic mice, but also now provides, for the first time, the appropriate context with which to begin to investigate the importance of the SM-MHC cis-elements shown to be important in regulation of this gene in cultured SMC. In addition, of practical significance, the SM-MHC promoter-intronic fragment herein disclosed represents the first genomic construct that exhibits complete SMC-restricted expression in vivo. As such, it may provide the basis for the design of SMC-specific gene targeting vectors for use in experimental animal models and for gene therapy in humans.

Furthermore, where a specific gene is known to be involved in an SMC-based disease, the gene can be operatively associated with an SM-MHC promoter/enhancer of the instant invention to produce an animal model of the disease. Examples of such genes might be those involved in hypertension or artherosclerosis. However, using the SM-MHC disclosed herein virtually any gene can be specifically expressed within SMC of a transgenic animal. In addition, the SM-MHC promoter/enhancer of the instant invention can be operatively associated with a gene which expresses a protein which can inhibit (a) other proteins or (b) transcription of other genes that further the diseased state being examined within the animal model. Alternatively, the SM-MHC promoter/enhancer can be operatively associated with an antisense gene, which could specifically inhibit expression of a gene within the animal model which may be involved in the diseased state. Using such animal models, one of skill in the art could test conventional drug therapies, identify key genes involved in the development of these diseases and/or develop a novel way of curing the disease.

The present invention further provides for recombinant DNA constructs which contain cell-specific, and developmental-specific, promoter fragments and functional portions thereof. As used herein, a functional portion of an SMC promoter/enhancer is capable of functioning as a tissue-specific promoter in SMC. The functionality of such sequences can be readily established by any method known in the art.

The manner of producing chimeric promoter constructions may be by any method well known in the art. For examples of approaches that can be used in such constructions, see, Fluhr et al., 1986, Science 232:1106–1112; Ellis et al., 1987, EMBO J. 6:11–16; Strittmatter & Chua, 1987, Proc. Natl. Acad. Sci. USA 84:8986–8990; Poulsen & Chua, 1988, Mol. Gen. Genet. 214:16–23; Comai et al., 1991, Plant Mol. Biol. 15:373–381; Aryan et al., 1991, Mol. Gen. Genet. 225:65–71.

Further, it may be desirable to include additional DNA sequences in the expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria or vacuole).

The following examples are included for illustrative purposes and are not intended to limit the scope of the invention.

6. EXAMPLE 1

Isolation and Cloning of the Rat SM-MHC Promoter/Enhancer

The SM-MHC gene contains a very short untranslated first exon (88 base pairs in rat) that is followed by a greater than 20 kb first intron. Babij P. et al., 1991, Proc. Natl. Acad. Sci., 88:10676. The cloning and sequence of the 5'-flanking region of the rat SM-MHC gene (−4229 to +88) has been previously reported. White S. L. et al., 1996, J. Biol. Chem., 271:15008–15017; Madsen C. S. et al., 1997, J. Biol. Chem., 272:6332–6340. To obtain 5'-flanking sequences with additional intronic DNA, a rat genomic phage library (Stratagene Corp. La Jolla, Calif.) was screened utilizing standard Southern blotting techniques, and a $^{32}$P-radiolabeled 45 mer oligonucleotide corresponding to the conserved untranslated first exon as a probe (nucleotides +14 to +58). One of the positive recombinant lambda phage clones identified contained an approximately 16 kb insert (determined by restriction enzyme and sequence analyses) that spanned the SM-MHC gene from −4,216 to +11,795. Identical restriction enzyme patterns between rat genomic DNA and multiple positive clones revealed that none of the clones identified had undergone rearrangement.

The nucleotide sequence of the rat clone which was used as the SM-MHC promoter/enhancer of the present invention is shown in FIGS. 8A–F. As noted on the Figure, the clone spans the rat MHC gene from position −4,216 in relation to the transcription start site (FIG. 8A) to position +11,795 (FIG. 8F) downstream of the transcription start site (FIG. 8B), thus, containing about 16,011 base pairs (FIG. 8F) in total. Furthermore, since the first exon of the rat MHC gene is 88 base pairs in length, the clone extends to +11,707 base pairs within the first intron.

Although the instant example describes the cloning and isolation of the rat SM-MHC promoter/enhancer, key regulatory regions within this polynucleotide sequence are known to be conserved across all species that express the gene. Thus, the instant invention encompasses not only the rat SM-MHC, but also the SM-MHC of other mammals, including, but not limited to, humans, rabbits and mice. The full length human SM-MHC gene sequence has previously been deposited with the Institute for Genomic Research in Rockville, Md., and is assigned Acc. No. U91323 and NID No. G2335056. It can be accessed at http://www.ncbi.nlm.nih.gov/htbin-post/Entrez/query?db=n_d. This sequence is hereby incorporated by reference in its entirety. Based upon a comparison of the human and rat SM-MHC gene sequences, FIG. 9 shows the high degree of homology that exists between the rat and human genes. In fact, as shown in FIG. 9, critical regulatory sequences are 100% conserved within the genes. Furthermore, it has previously been shown that similar regulatory sequences are conserved in the rabbit and mouse genes for SM-MHC. See, Madsen et al., 1997, J. Biol. Chem. 272:6332.

EXAMPLE 2

Construction of the Rat SM-MHC-lacZ Reporters

To facilitate removal of pBS plasmid DNA from the pBS-lacZ vector, the pBS-lacZ vector was modified by inserting Not I restriction enzyme recognition sites at the HindIII and EcoRI sites located at the borders of the pBS vector sequence. Two SM-MHC-lacZ reporter genes were constructed for the generation of transgenic mice. One construct (p4.2-lacZ) was created by ligating about a 4.3 kb BglII fragment that extended from −4220 to +88 into a unique BamHI site of the pBS-lac-Z vector, and the other construct tested (p4.2-Intron-lacZ) was generated by subcloning an approximately 16 kb SalI fragment that extended from −4229 to about +11,700 into the SalI site of the pBS-lacZ vector. To facilitate splicing of the p4.2-Intron-lacZ construct, a synthetic splice acceptor site was ligated into the KpnI site of the pBS-lacZ vector prior to insertion of the SM-MHC DNA fragment. The location of the KpnI site, between the SalI site and the lacZ gene, allowed for the correct positioning of the splice acceptor site at the +11,700 end of the SM-MHC intron. The proper construction of each SM-MHC-lacZ chimeric plasmid was verified by sequencing and restriction enzyme analyses. As an additional precaution against cloning artifacts, both transgenic constructs were tested for lacZ expression in transient transfection assays in cultured rat aortic SMC using a method that was previously described. Madsen C. S. et al., 1997, *J. Biol. Chem.*, 272:6332–6340. In this assay, both constructs were determined to be positive for lacZ expression.

EXAMPLE 3

Generation and Analysis of Transgenic Mice

Plasmid constructs p4.2-lacZ and p4.2-Intron-lacZ were tested for SM-MHC promoter activity in transgenic mice following removal of the pBS vector DNA through NotI digestion and subsequent agarose gel purification. Transgenic mice were generated using standard methods (Li L. et al., 1996, *J. Cell. Biol.*, 132:849–859; Gordon J. W. et al., 1981, *Science*, 214:1244–1246) either commercially (DNX, Princeton, N.J.) or within the Transgenic Core Facility at The University of Virginia. Transgenic mice were either sacrificed and analyzed during embryological development (transient transgenics), or were utilized to establish breeding founder lines (stable transgenics). Transgene presence was assayed by the polymerase chain reaction using genomic DNA purified from either placental tissue (embryonic mice) or from tail clips (adult mice) according to the method of Vernet M. et al., 1993, *Methods Enzymol.* 225:434–451. Transgene expression and histological analyses were done as described previously. Li L. et al., 1996, *J. Cell. Biol.*, 132:849–859; Cheng T. C. et al., 1993, *Science*, 261:215–218.

EXAMPLE 4

SM-MHC Immunohistochemistry

Various smooth muscle containing tissues were collected from 5–6 week old transgenic mice and fixed overnight in methacarn (60% methanol, 30% chloroform, 10% glacial acetic acid). Tissues were subsequently dehydrated through a graded series of methanol dilutions. Fixed, dehydrated tissues were prepared for paraffin embedding by incubation in 100% xylene. Tissue was then infiltrated by incubation through a series of xylene:paraffin(3:1,1:1,1:3) solutions, and two final incubations in 100% paraffin prior to embedding in 100% paraffin. Serial sections (6 μm) were dried on uncoated slides, and then dried for approximately 45 minutes on a slide warmer set at 40° C. Sections were cleared in multiple washes of 100% xylene, and re-hydrated through a graded ethanol series to a final incubation in phosphate buffered saline (PBS). Endogenous peroxidase activity was quenched by incubating slides in methanol containing 0.3% hydrogen peroxide for 30 min. Slides were subsequently rehydrated in PBS and blocked in a 1:50 solution of normal goat serum made up in PBS. Sections were then incubated with the primary antibody for 1 hr and washed with 3 changes of PBS. Detection of primary antibody was performed using a Vectastain ABC Kit according to the instructions of the manufacturer with diaminobenzidine (DAB) as the chromagen (Vector Laboratories, Burlingame, Calif.).

Antibodies: Several different SM-MHC antibodies were employed. These included a monoclonal antibody designated 9A9 which has been previously characterized (Price R. J. et al., 1994, *Circ. Res.*, 75:520–527) that shows reactivity with the SM-1 and SM-2 isoforms of SM-MHC but which shows no reactivity with non-muscle myosin heavy chains or other proteins. However, whereas this antibody showed some reactivity with mouse SM-MHC isoforms in Western analyses, it reacted very poorly with mouse SM-MHC in fixed tissues. In addition, although a polyclonal SM-MHC peptide antibody provided by Nagai R. et al., 1989, *J. Biol. Chem.*, 264:9734–9737, showed complete specificity for SM-MHC isoforms in Western analyses of smooth muscle tissues from multiple species, it showed little or no reactivity with mouse SM-MHC isoforms. To circumvent these limitations, a rabbit anti-chicken gizzard SM-MHC polyclonal antibody was employed. The rabbit anti-chicken gizzard SM-MHC antibody was made by immunization of rabbits with partially purified gizzard SM-MHC as described by Groschel-Stewart, 1976, *Histochemistry* 46:229–236. However, based on Western analyses, it was determined that this antibody showed reactivity with both SM-1 and SM-2 MHC, as well as with non-muscle myosin B (or SMEMB), as did a number of other "smooth muscle myosin" antibodies tested, including one from Sigma [designated hSM-V] (Frid M. G. et al., 1993, *J. Vasc. Res.*, ;30:279–292) and one from R. S. Adelstein (Schndider M. D. et al., 1985, *J. Cell. Biol.*, 101:66). As such, staining with these antibodies in tissues that express both SMEMB and SM-MHC is equivocal. However, adult mouse aortic SMC, like those in other species (Rovner A. S. et al., 1986, *J. Biol. Chem.*, 261:14740–14745; Rovner A. S. et al., 1986, *Am. J. Physiol.*, 250:c861–c870; Phillips C. L. et al., 1995, *J. Muscle Res. & Cell Motility*, 16:379–389) were not found to express SMEMB based on Western analyses. The rabbit anti-chicken gizzard SM-MHC polyclonal antibody was used at a concentration of approximately 20 μg/ml in PBS. Biotinylated goat anti-rabbit secondary antibodies were purchased from Vector Laboratories (Burlingame, Calif.) and used at a concentration of 10 μg/ml in PBS. Appropriate Western analyses, and immunohistological controls were performed to assess specificity, including exclusion of primary antibody, and use of control non-immuni rabbit serum.

EXAMPLE 5

Expression of the SM-MHC-lacZ Reporter Gene in Transgenic Mice

It has previously been reported that a SM-MHC promoter DNA fragment extending from −4220 to +88 was capable of directing high-level expression in cultured rat aortic SMC. Madsen C. S. et al., 1997, *J. Biol. Chem.*, 272:6332–6340. When tested in bovine endothelial cells, L6 myoblasts and L6 myotubes, the activity of this construct was determined to be negligible. To determine if this same promoter/DNA fragment was capable of directing SMC-specific expression in vivo, this fragment was sub-cloned into a pBS-lacZ reporter gene construct (p4.2-lacZ) and tested for activity in transgenic mice. Thirteen independent transient mice harboring the p4.2-lacZ transgene were generated and analyzed for lacZ expression at multiple embryological stages ranging from embryonic day ("E") 13.5 to 19.5. No transgene expression was detected in any of the transgenic mice. These data suggest that, in contrast to activity levels observed for cultured SMC, the SM-MHC promoter fragment present within the p4.2-lacZ construct did not contain sufficient DNA for directing SMC-specific expression in transgenic mice.

EXAMPLE 6

Portions of the SM-MHC First Intron were Required for Directing SMC-Specific Expression in Transgenic Mice It is well documented that cis-elements important for gene expression can be found outside the 5'-flanking region. Furthermore, they can be found within intronic regions. Because 4.2 kb of 5'-flanking DNA was found to be insufficient for expression in vivo, a larger construct with added intronic sequences was tested. A rat genomic phage library was screened and one recombinant clone was identified whose insert contained 4216 bp of 5'-flanking region, 88 bp of the first exon, which is untranslated sequence, and an additional 11,795 base pairs of first intronic sequence (total span: −4,216 to +11,795). This fragment, which was essentially identical to the p4.2-lacZ construct with respect to the 5'-flanking sequence and with respect to the presence of the 88 bp of 5' untranslated sequence, was isolated from the lambda phage by SalI digestion and sub-cloned into the pBS-lacZ vector to create the SM-MHC-reporter gene plasmid p4.2-Intron-lacZ.

The reporter gene p4.2-lacZ was used to generate four independent transgenic mice; one mouse was sacrificed at E13.5 for transgene expression analysis, and the other three were established as stable transgenic founder lines (designated as 2282, 2642 and 2820) that were utilized for analysis of transgene throughout embryological development and early adulthood. Analysis of adult mice generated from the three stable founder lines showed that lacZ transgene expression was essentially identical between the three founders and completely restricted to smooth muscle (FIG. 1). Gross examination of the heart and lung region excised from a 5 week-old p4.2-Intron-lacZ mouse revealed that transgene expression was present in the descending thoracic aorta, coronary arteries, trachea and bronchi (FIG. 1, Panel A). Transgene expression was not detected in any non-smooth muscle tissues in this region, such as heart muscle and lung tissue. Of note, transgene expression also was not detected in several smooth muscle containing tissues in this region including the esophagus and branches of the pulmonary artery, although expression was seen in the pulmonary artery outflow tract. Transgene expression was readily detectable in the major branches of the coronary arterial tree including the left and right coronary arteries (FIG. 1, Panel B), as well as the small coronary arteries and arterioles (FIG. 1, Panel D) of 5–6 week old transgenic mice. However, no lacZ expression could be detected in any of the coronary veins (FIG. 1, Panels B and D; and FIG. 1, Panel C). Transgene expression also was readily detected in the descending thoracic aorta, and intercostal arteries (FIG. 1, Panel C), as well as throughout blood vessels in the extremities and main body trunk, including small arteries, arterioles and veins such as the mesentery vessels (FIG. 1, Panel E). Expression of the lacZ transgene was readily detectable also in the visceral smooth muscle of the intestine (FIG. 1, Panel F), the ureter and bladder (FIG. 1, Panel G), the stomach (FIG. 1, Panel H) and the uterus and gallbladder. Thus, these initial analyses demonstrated that the p4.2-Intron-lacZ construct contained sufficient DNA for expression in all SMC tissue types, although certain SMC tissues were negative, at least in 5–6 week old animals. Moreover, certain smooth muscle tissues such as the aorta (FIG. 1, Panel C), intercostal arteries (FIG. 1, Panel C), jejunum (FIG. 1, Panel F) and stomach (FIG. 1, Panel H) clearly showed a mosaic pattern of transgene expression that was visible even at the gross tissue level.

To assess transgene expression at the cellular level, a histological analysis of lacZ reporter expression was performed (FIG. 2). Results of these studies further demonstrated that transgene expression was highly restrictive to smooth muscle. For example, analysis of the bladder and airway smooth muscle (FIG. 2, Panel A) showed that transgene expression was highly specific and appeared to be present in virtually all SMC located within these tissues. Likewise, SMC within many smooth muscle tissues including the aorta (FIG. 2, Panel B), coronary vessels (FIG. 2, Panel C), the intestine (FIG. 2, Panel D), stomach and many smaller blood vessels including small arteries, arterioles, veins, and venules (FIG. 2, Panels E and F) showed clear evidence of expression of the transgene within SMC, although some heterogeneity of expression was evident between adjacent cells. Taken together, these results indicate that although the p4.2-Intron-lacZ transgene exhibited SMC-specific activity and was expressed in all major SMC types, it exhibited differences in activity in subsets of SMC both within and between different adult SMC tissues. Nevertheless, expression of the p4.2-Intron-lacZ transgene was present only in SMC, and not in any non-SMC.

EXAMPLE 7

Transgene Expression in the Developing Embryo

To determine if expression of the p4.2-Intron-lacZ transgene resembled the developmental expression pattern of the endogenous SM-MHC gene, embryos from the three stable founder lines were obtained at various stages throughout development [embryonic day E10.5 through E19.5] and analyzed for lacZ expression. Additionally, one transient founder was generated and analyzed for transgene expression at E13.5. With the exception of transient expression in the heart (B12.5 to E17.5) of one of the stable lines which was localized to the myocardium, transgene expression patterns were essentially identical in all four independent transgenic lines (i.e. one transient transgenic mouse and three stable founder lines), and restricted to SMC. Transgene expression patterns of embryos derived from stable founder lines 2282, 2642 and 2820 are presented in FIGS. 4 and 5. The earliest developmental stage at which transgene expression could be detected was E12.5, where lacZ expression was readily identified in the trachea and bronchi (FIG. 3, Panels A and B). By E14.5, transgene expression was detectable in the bronchi, intestine, stomach, trachea and the aorta as well as a few other vessels throughout the embryo (FIG. 3, Panel C). Of particular interest, although transgene expression was virtually absent in the esophagus in the adult (FIG. 1, Panel H), its expression was clearly evident in embryos. At E16.5 transgene expression was more pronounced in the aorta than at earlier developmental time points, although it had a variegated and less intense appearance relative to other smooth muscle tissues (FIG. 3, Panel D). Additionally, the frequency of vessels that were positive for transgene expression was higher in peripheral vessels, and particularly those located in the extremities of the animal.

One of the most notable differences between the E16.5 and E19.5 embryos was a marked increase in the frequency of vessels that stained positive for lacZ expression (FIG. 4). However, lacZ expression remained undetectable in a number of vessels. Especially conspicuous was the general absence of expression in the large blood vessels in the head and neck region including the internal and external carotid arteries, the jugular vein and the cerebral arteries and veins. However, many smaller sized blood vessels were positive for transgene expression in the head and neck region. Transgene expression was readily detectable also in many other arteries and veins throughout the body including the iliacs (FIG. 4, Panel D), the caudal artery and vein, the femoral artery, the umbilical artery and vein, the ulnar and radial arteries and superficial arterioles and venules within the musculature of the thoracic cage (FIG. 4, Panel E).

Although expression levels in these types of studies are not quantitative, it is worth noting that levels of lacZ staining within the aorta did not appear to be as intense as compared to many other blood vessels and visceral smooth muscle tissues. In summary, results of these embryological studies support the data gathered from analysis of transgene expression in juvenile and adult mice, and indicate that p4.2-Intron-lacZ contains sufficient DNA for directing SMC-specific expression in all SMC-tissue types. However, results leave open the possibility that additional genomic regions may be required for SM-MHC expression in some subsets of SMC. Nevertheless, these results demonstrate that the p4.2-Intron-lacZ transgene is capable of conferring SMC-specific gene expression in vivo.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of expressing a polynucleotide in a smooth muscle cell in vitro comprising, introducing into said smooth muscle cell said polynucleotide in operative association with a SM-MHC promoter/enhancer, wherein the SM-MHC promoter enhancer is selected from the group consisting of
a polynucleotide comprising about +89 to about +11.7 kb with respect to the transcription start site of a rat myosin heavy chain gene; and
a human SM-MHC promoter/enhancer, wherein the human promoter/enhancer comprises sufficient sequence from the first intron of the human SM MHC gene to confer SMC-specific expression in vivo.

2. An isolated SM-MHC promoter/enhancer comprising a portion of a rat myosin heavy chain gene wherein said promoter/enhancer is capable of conferring SMC specific expression in vivo and wherein the portion consists of a sequence from about −4.2 kb to about +11.7 kb with respect to the transcription start site of said rat myosin heavy chain gene.

3. An isolated SM-MHC promoter/enhancer comprising a portion of a rat myosin heavy chain gene wherein said promoter/enhancer is capable of conferring SMC specific expression in vivo and wherein the portion consists of a sequence from about +1 kb to about +11.7 kb with respect to the transcription start site of said rat myosin heavy chain gene.

4. The SM-MHC promoter/enhancer of claim 3, wherein said portion consists of a sequence from about +89 to about +11.7 kb with respect to the transcription start site of said rat myosin heavy chain gene.

5. An isolated polynucleotide comprising a human SM-MHC promoter/enhancer in operable association with a heterologous polynucleotide, wherein the promoter/enhancer comprises sufficient sequence from the first intron of the human SM MHC gene to confer SMC-specific expression in vivo.

6. The isolated polynucleotide of claim 5, wherein the promoter/enhancer further comprises a CArG1, CArG2, CArG3 and GC Repressor sequence.

7. A vector comprising the polynucleotide of claim 5.

8. An isolated cell comprising the vector of claim 7.

* * * * *

SEQUENCE LISTING

<160> NUMBER OF SEQ ID NOS: 3

<210> SEQ ID NO 1
<211> LENGTH: 257
<212> TYPE: DNA
<213> ORGANISM: Rattus norvegicus

<400> SEQUENCE: 1

```
gggaggctgc agggaccata tttagtcagg gggagccaga gccccgctgg tatgccaagc      60
tgggaattct tgtttcgaga attgcgcctg gccttttggg gctgtttccc gcccaggccc     120
aggaggggga ccagctcagg acctcgaggg tccgtgcgcg gggagcgagg ctccccggcc     180
tggcatgagg ccactctgcc tcgacttcct tttatggcct gagtgtgagt gcatggagag     240
tgggagggag ggaggga                                                    257
```

<210> SEQ ID NO 2
<211> LENGTH: 120
<212> TYPE: DNA
<213> ORGANISM: Homo sapiens

<400> SEQUENCE: 2

```
accacgcaga ggcagaggcc ccgccgtccc gccgctcccg ggcgcccggc cgcccggaac      60
ctcggagact gtgcccgcgg ggagcggagc gcccgggctg cccgcggcgg ccactcgcac     120
```

<210> SEQ ID NO 3
<211> LENGTH: 16011
<212> TYPE: DNA
<213> ORGANISM: Rattus norvegicus

<400> SEQUENCE: 3

```
agatcttaaa acacatcaac ctgggctgag gggatgtgtg tctctgtgtc tgtgtatgca      60
catgcatttg aggccagatg aaaatgtcag atgtcctctc actgctttat tcccttgaga     120
cagggtccct cactgaactt gttggagcta tgctggtagc cagcaagccc cagtggcctt     180
cctgtctcta tctcacacag cacaatatgt gtggccatgc tccactttt tacatggaaa      240
```

-continued

```
ttgggtcctt ccaactgggg ttctcatttg tgcagtgaca ctcttcccca ctgagccatc    300
tcctcaggcc agctgatata ttttaaata attaaatatt tagcacatgc ctttagaagc     360
caatagctat ttaaagctgt ttgcttaaaa aaaaaaaaa aaaaaagact tcattatccc     420
aacacttatg agggagagac aataattcca aaccagaac cagccagggt acacagtgag     480
actttattta aaaaaaaaaa aaaagaaag aagaaaaaa aaagaaaaa gaaaaaaaa        540 ggctccaaag agaaatttcc ccttcatcat ctaatcacaa gaaaacaatt tatttatttt    600
gacatcactc agtccaaagg agcttttgt aaagtgactt ctcttcttaa aataagtgac     660
ccttcccaac caccaaaaac aaaacagaaa cctctgccct gttctagagt ccttttgaag    720
acttcagata cctgaagagt ggacagatat ttaccgagtg acttaaatga acatactgtc    780
cctgggtact gctcaagcat gccaggagag catggatggt ttatgcaagg ctggcactgt    840
cattaacaac tcagtaaggc ggagaagaca gagagcctct cctaagacaa tggcacataa    900
ggacatgggt aacccagag gttcccggct agtacttagc agagctgaga tcagacttgg     960
gcctctgtgc tcgcttgcct agtgggcaac actcaagact ggggtaaaca ataagttgat   1020
ctgggatatg gctcagtaat cacactgaga attcaacact gggaaggcag aggaggatcc   1080
ctgggattgc tgcctggctc tctagcagcc tagcagaatc aacaaactcc aggttcagtg   1140
agagatgctc acaaaataaa atggaggagc aactgaacac actcagtgtt gacccacaca   1200
cacactaaag aacacgtgta ccacacagac acagacacag gataacctac ccatgttgtg   1260 tatgactca gccagcccag gttggaaact cagttcctct gttaactctt ttcaaacctg    1320
ggtcctcagc gatgtgctgg ggaacctact tcacggcatt attctgggca ttagatgtaa   1380
aggaagcagt aaagtttccc tttcttgac tgaggtgatg cgagaatgag ggcctgaatt    1440
ccatctctag gactcacata agacaccca gactgcactg gccagtaagc ctcacctatg    1500
cctccaagcc tggctgtgag agactgtctc aaaaacaaag taaaacaac aaaatcaatg    1560 tcagatgtgc acacatcgaa tcccagcatg tgtacggcat gcttgcagtc agccttgttt   1620
acagagagtt ctaggccaac cagctataca cagtgagacc ctgtggtaga cggctcctaa   1680
gaactgacat ttgtgactga cagatgtgca catctaccac atgcacatca cagtttccat   1740
tttacaaaaa ggttaacact tactaattga ttagggagtg gggcacccca ctgctacatg   1800
tgaaagccag agaatgatgt gttccagtcg gtcagttgtg tccttccacc atgtaggtcc   1860
taaaaatgga actcaaggca gtcttggcag caagtgcttt atccatagtg ccatcttatt   1920
ggcccagtct cctataatg aaattatttg tgtttccaag ttgatgtaat tcttaaaaa     1980 tcagctgtgc tccttggagt ttgacttcac tgaagcctgc tacaggagtg cccttccttc   2040
ctagcactag gatggccagc tctgggctgg tttcagacta gggtaggtgc aggtgggccc   2100
tgggcttccc tccttcattc ctcctgggct caatgccaag ccggtttcca ttcctttac    2160 gtgcactgcg aagaggcttt ggggaagcgg cctcatccat catgcagaga gctcctcccc   2220
cacctctaca gagagccagc caagctgctg tccttggctc tgctctgtcc accctgtgag   2280
gaggctggga tgaggttggg gatggggagg atcaggattc agatgttttc aagtctgaga   2340
agcaggtgag cttggtccta aagaatatg gaagggtct actggggttg agatatagat    2400
cactgtatca aagtcaacag gggggctgtg tggcttttc atatcccaaa gtcagcttgg    2460
tgctggtttc ctaggcttcc tgagtccgac aaaggtgcag tgtgttaatc tcacaccact   2520
tcaaggactg ttacaaaaaa aaaataggaa ggagctcgat tcgcccttt ttacaggcag    2580 ggtaactaag agccagtact tgcccatggt cctgctgtta taaagaggct cagtagactc   2640
```

```
ccattcaaac aactgtgctc agaggccttc tgtcgtcctg tggccaattc ccctattgct   2700
ctctggagtg aatattggga tattaaacag tactgacctt gctgaggacc ctcagggtac   2760
tcagctcttc tggcctgcaa aatggggctg gacaggttg gccaggatca tcctctggtt    2820
gggagaacca gctgcacgtg ggtctggagc tcttattagt actgggtcc ccataacgct    2880 ccatgggctc agcggggagc tgcacgggac catatttagt caggggagc cagagccccg    2940 ctggtatgcc aagctgggaa ttcttgtttc gagaattgcg cctggccttt ttggggttgtt  3000 tcccgcccag gcccaggagg gaggaccagc tcaggacctc gagggtccgt gcgcggggag   3060
cgaggcgtcc ccggcctggc atgaggccaa ctctgcctcg acttcctttt atggcctgag   3120
tgtgagtgca tggagagtgg gagggaggga gggagagagg gaggaaagaa agcggggtgg   3180
gggggtgggg gggtgggggg gtgggggggt gcggagagca gagacagaga cagagagaca   3240
gagagacaca cagagagaga cagagagaca gagagacaca cagagagaga cagagacaga   3300
cacacacaga gagagacaga cagacaaaga gagagacaga gacagagaga cacacacaga   3360
gagacagaca gacaaaaaga gaagagagac agagacttta gggacgtaat catcacaggg   3420
aaatcaaagc taagagtgtg atgaaaagag tgtcaggtca gacaaaagag acaggggcca   3480
agatccgtac agggctaagg gacacagaga ttgagaacac cgagtggtaa ggggggcagc   3540
tgacagcagg tcccccacat tctcttagag tcttagcatg catcctccaa gtgccataac   3600
gcagtagcaa cccgcttttc aacgatgctc agagaaacca tgttattggt cccaggcacc   3660
ccggttgtag ggtgaaagga gctgcagaga acaagttgga aaaacaagtt tcccagcagt   3720
cacagaggat atgcagtgac tgtgccgact tgtttttttt tttttaagtc cccttccccc   3780
cccccgcccc gccccccggct tgctaagcac aaccggcttc gaatcttagg aagtggcagg   3840
cgaatgaaga ggggatgagg gagagagggt ggcatcaagt ctccagtatg tatgaacaga   3900
aagaggttaa aatccagctg gaatggacct aggggaagaa attctcaagt ctccctacag   3960
actctgaaca ccgaatccct tttctctaag gacgcaggat ctgggtggct gcagggagcg   4020
aggcctgagc ctgtgggtca acttgccagc agcccccctg cgcctgcgct aggtggttcc   4080
cagaggctct gttcctcacc tgcagggggc gctgggaagg gcagaggacc ctcccacccc   4140
gcccggcagt cacctccccct tccccaccct cgggtagcgc tgactctata aagccagatg   4200
tccgaagcat acagagagat ttggaccatc ccagcctggg atcagtgtca gatccgagct   4260
ctccatccgg tgttctcctg ctagtccacc ccagtagcag atctgtaagt agaagttgat   4320
cccttagggg caagcctggg cggtgagctt gagcagcttc taaaacatcc tccagggagt   4380
ggggacccca aggggttctg attgtcatct cttataagga cagtgggaag aagcccggta   4440
caggaccacc ctagacctcc cgtgattact cccattctcc gcaccaaacc agcatcctca   4500
ggttgcctat gaacagaacc acctgggaaa gtggggtagg taattaaagg ttctggccac   4560
tgggcccaat tccaggtatt ttaagactac agtctaaaaa gcaaacaaaa tggcctactt   4620
aaaaactaac tagtgacaca gtggacaagt gaactgtggt ggaaactgtg ggtctgaatt   4680
caaataccag tattgaaaat aataagaagt ctgggataaa tatccactga acatccccag   4740
aatactcaaa acatgggtta aagtttaatg actctgaaca caggccgtgt gttcttattc   4800
cactcctaat ggaatgtgct gttgaaaatt tactggtaaa caaaaatgct taatgttaaa   4860
taaggtcgtt tcttcctctg ttacttccaa aacacaaatc tccattaaaa aggaaccttc   4920
tccagtttgg ttgggccccc agatgcccag gtgggtgctg aggctccatt tgcatccccc   4980
```

-continued

```
acactgagtg agcagacgat ggattttggg gctcctcagt gggaaggtta ctctcaggtc   5040
agggagagga gctagcagag aaatttatgc tattccagtt cagaattgga gaagtcttgc   5100
catgtccaga aagcaccctt caaagttatg tctgtcagag aacagaaaaa ttttttttga   5160
aagccaggac aaggctgctt tggttctact actaagaact gaaaaactgc tgacttgctg   5220
ggaaagaagg aaatccggtt gtgtttggta aactactctg cttcgttggt ttcctggggg   5280
aggttttttt ttagttcagt aattcaatat gctattttag actcaaagaa agacaggtct   5340
gaaagtctct cataacaaga aacactttct cttttatgat gttgttgatg gcacacttaa   5400
caagccaggt gctttaacag cgtttagatg gaactgggtt cttttaatca tcatatacac   5460
cttaccttgt cttgacatct ctgttttttcc caaaaccaaa atttgttgga ctcctgtttc   5520
tgatggattc agtgtttcca gcttccatca cttttttgaag aagattgaaa ctgatctttt   5580
accaatttaa aatgacagag actgtctttt aaattttgtt gatgttgttg tttccctgtg   5640
gatgtggtag ggttccagga ggctggcgtg atctcaaaca tgcctgggcc aagccaccct   5700
ggagaaacct ggacttttat tatcagatct gaaatagagc ctcttccgta caaggtagtc   5760
actatggatt tatcattact tttctgtggg aggctgggct ggaggcagac atgcccttgt   5820
atggtagtgt tttctatgag gccattccca gtccccccttg gccaatcacc cagccttttcg   5880 atgcagcctg actggcttga gttctgggta cttctctgtc tttccctgta gagatggaca   5940
atgaagttct tttttttcctc tcttttcttg tttggaagtt ctatttgtat ttttttggtg   6000
gaaattatat tccacatatc taataagaac gggtggtgtt tacatctaat aaaccattga   6060
ataattttga aacaggataa agacgatcct tttagaaaac tatatcccgt ttcaaatact   6120
cagaatcagg tcttaaccac attattttgc caggtatggt ggcttgtgtc taaaatacta   6180
gcacttggga ggctaaagca agagagtttg aggctaacct ggactgcata gcaagttcag   6240
gccatcctgg actacagtgg gaaacactat cttggaaaaa ataaaaaata aaatcaaaa   6300 cccagcctaa tggtacataa cttcaattcc agcatctgag gtaaaccagg aagcacagct   6360
gattaatgaa cccaaagtca gcctgggcta cctaaggaat cctatctttt acaatttgtt   6420
gatgctgttg tcattttcct gatcactttc ccatctgcag aatgggactg ttgagaacag   6480
ccagcgtgtt aatgtttctg tagcacttgc ttagtcttct gagaagtaga agatcactta   6540
gctagggttt gatccccatg actgcagcaa aagaggaaga ctcattaatt ggagtcttca   6600
cagtagccct tggaaccaat actaatagtc ttcactccat ttcataaatg tgggctttga   6660
aaactttgtt ctgtctataa aagatggggg ctcttacaaa ctaagcttct tgtaactcca   6720
gagcctaatg ccccttttggg agctttcaat agataaccca tgtgaagggt ctgacacaag   6780
gctggcacca gcaaagttca gcagatggta atttatagta atatgactag ggacgcttaa   6840
gagcatattc tgtatgacac agctgatatc aagaaaccca aacggtggcc ttttcccctaa   6900 agcagaaact caccccctaat tttcctttag tgtaaatctc atagtggatt ctttgctccc   6960
tggttctctt tctgtcacta gtgaccttt agttacattg atctataggc ttcaaggacc   7020
aggaggcaca gagtcaagag aaaggcaagc aagaatttga agggagaagg aaaccgctca   7080
gcactgtagc aaggggaggt caggctacca tgatgctcct gcgcttcagg gaattatcct   7140
ctcagaatgg ccaacagggt agggacctgg cctgttccac tcaggcccat ttgaactttc   7200
tttctgttct atgggtccct acagatgaat tcagcccact gtagactgga agttcatctt   7260
taacagcatc caaacggaac acatacagac cttctttctt gtcactgtcc ctgagtcaag   7320
cagcataaga actatgtctg ccaacctgcg aggggaagtt gctcaagatg ctatgcaaac   7380
```

-continued

```
actccagctt tccatggaag ggacttcagc atctatggat ggtggtagca aagcactcct   7440
caagctgatc aaagaatagc tgtcccttcc tgcccctccc ctaatgaagc gtgcagtcag   7500
tgacagagac ctcagaaatg tcttaggtca ccaaaggtca ttcttgccat cccaggctcc   7560
agattagcat tttctccctt tttatttccc tccattttgc ctgtctgcat atgcactact   7620
aacaaacatt cttctttct ttttttttt tttcttggag ctggggactg aacccagggc    7680
cttgcgcttg ctaggcaagc gctctaccac tgagctaaat ccccagcccc gctaacaaac   7740
attcttaaat agaattctaa attttttaaa gtcaaatttc cctttactc aaaccctggc    7800
attttacaaa acatttttca ccttatcaca aatcttcact atcttttcta tatctttata   7860
tcattgtatg ttacttttta tctgctacgt agtattctgt tacgtattta ataaaatata   7920
cttggtgcat gatgccatgt ataaatggcg cttggggaag tacccgtgta ctagttgact   7980
gttgcccatc agaaatgccc aggaccagaa atgttccaga gttttctttt cttttaaatt   8040
ctttttgatt ttgggatatt tgcacataaa taattatata tttgtatata aataatgata   8100
tatcctggaa acgagcacta attcttttgt tgcctgtctt ctgggttttt tttttttctt   8160
tccttctttc tttttgttct tggccatcct ggagctctct gtagaccagg ttgtgcttga   8220
actatagaga tcctcctgcc tctgcctccc acatgctaag actaaaggca agagccatca   8280
cacccatctg tgagcacaaa tcttgatatt tcacctttgc tttatacaga tggttgtata   8340
gtcagtcgtt gtattcgatg tttttaattc tacattttca ctgtgacctg ctacatgaaa   8400
ttcaaataca aacttgtcca ctcacacaat attggccctc aaaaagctgt gagcctttga   8460
acttttgggg ttaagaatgt ttagcttgta tccgtattct tcgcttgtaa actctcttcc   8520
tgtaatcaca tgagttccta gcaaagaggt gaatagatag cacattggga atcagcatct   8580
gtctctaaat ggtctttgaa agaaactgta gatacctgcc tggaccagcc agacctgtgt   8640
cttagcacct attttaaaca ttgttctacc tgagttgtaa gatgcaaaac atagtggggc   8700
tctgagggcc caaaggccct gaacaggggt gacctcagtt gtgtggaata gggagaaaga   8760
cagcagaagg aagggaggaa agacgggcaa ggaggggaag tgttcatgt gtatggctgc     8820
atctaaatag aagccatgaa gactagctat tgtttctcag gtccttccaa cttgcttttg   8880
gagacaggaa ccctcaccag cctggaactt gccaagtagc taattggctg gctcttgacc   8940
cctagatctc tttcccctcc actctaacgt tacaacatac agctctctct ctctctctct   9000
ctctctctct ctctctctct ctctctctct ctcattttat tttttaaaaa aaatttattt   9060
atttatttat ttatttattt atttatttat ttatttattt catggatgta ataccgtcc    9120
tgtctcaacc ccaaaatggg catcggatcc cattccagat ggttgtgagc caccatgtgg   9180
ttgctgggaa ttgaactcag gacctctggg agagcagtca gtactcttaa tgctgagcca   9240
tctctctagc ccttttccccc tcttctaaaa catagttttt gaagatctaa cgcagatctt   9300
caagtgtcag tatggcaagc actttgctga ctcaccagcc catgaccttc tcccttaatc   9360
tccaaatcct tttagtggga gagacacaat cgttttactt tagccattgg aaagagcttc   9420
cttctaaagc agcttgaaaa gccattgggg tttccagcgt gtgtgtggca gtgttaccag   9480
gttattgtga tgggacaagt tcttattctc tttcttctga ggaggtaccc tggagacctt   9540
ggggaagtgg gggtggtagg gaggtttatg gcattggggc agggagtgaa gaagagattt   9600
actgctgaga gcaaaaggat tgttagatcc aacaatctaa caaaaaaggt caaacttttt   9660
tttctttat gaccttagtt gtgataacag aaaaatagta atgtaagtga tgtccacttc    9720
```

-continued

```
acagaatcct cataagatat tcaagaccat aaatgtgggc cactcttact ttgatgccca    9780
gtaggggggcc cctgagcaga tgcagcttag ttaataggat gcttgcccac catgttttgt   9840
acatgttcca ccctcagtac acagccaggc atcgtaggaa acacttgtag ccccctagcac   9900
ttggcgggag gaccaagagt tcaagtccgt ttttgattat gtagtgagtt cagggttagc    9960
atgggctata ggagactgta gagggctatg tgattaagaa cagatttgag ccccacaggg   10020
ctcctggtgc agcatgagtt tgaggaacta gtgtgtatag catgcttttc cttcttcttg   10080
gtatgtcaag tgactttcta gacgcagatg tggcatcgaa ctagaactaa cattattggg   10140
gcctcttttgg attgcttact gagctgcagc tttggctcca agaacttatt atggagatgg   10200
gcatggtggt aacaactaca ctacagaaga ctactacttt gagaccagcc tgtaccagag   10260
cctggtggat acagctcaat gggagaacac atattgagca tgtacaagtc ctgagttcga   10320
tcttcagtac ctcgaatatt ggccaactaa aaggaatgaa tttaggggtg ggaataaagt   10380
tcagatagta gagtgtctgg ctagcattca caaagcccca agtttgacct ccagcactcc   10440
agaacctgga tgtggtagag tacatctatg atcccagcac tcaggagaac ttcaaagtta   10500
ttccaagcta cataataata caagaccagc ctgggctaca caagatctta tctcaaaaag   10560
ctttggtttc aaactgggga cagttttccc tctgggagtg atatctagca gtgtctggac   10620
ctccttttga tgtcatgact aggaaatggt ggatactggc atagagtggg ctgaactcac   10680
actgaacagc accagagaac cagccagtgc caaggccaat agtacagggg ctgagaaaat   10740
ccactgtaaa tcaggagtca gaacaggacc aggagttaga aaaccaaatg ttacttcagc   10800
ctgtcttgtg ggtctttaat ggcattgtga ttttggttct agtcatcatt tcttttcggt   10860
attgagattt gaactagggt cttgtgcatg ctaagtaaga actctgccac tgtgccatat   10920
cccaacctat gtggttgttt tgtatcaggg tctctccttg taacccaata ctcaaaccca   10980
tcatctcctt catcatggga ctacatatgt gagcagtttt actgttttc cttcttcctt   11040
gtgttttacg caatacctgt cctgatattt cttgctgtat tgtcactgtc ccatcttttg   11100
aaaatttcag gctctgaaca gaaatgaagc aaatcttctg acagtaaatg gagttccctg   11160
aacttccaaa ctgccagaca gaagcagaat gtgtcctctg tatgcctgta atttttttctg   11220
tccttgagtt ctctgcctgc ctcctctaaa ttctaaaaaa agaaagagca aaaacaaaca   11280
gacaataaaa aaacttgcaa cttttttcag aagccacaag actgtaaaag gaccaacaaa   11340
ctgctttgcc tctgtgtgcc ttggtttctc attggtaaag gaatggtaac atctttcctg   11400
ggttgttttg caatgctggg gatagaatcc agggcttaga gtatattagg ttccctgcct   11460
ctaaactata ttctctagtc ttaaaagtat tgtttgcatt gttactgtgt tttatggtgg   11520
ggggatggga acccagggac tgtagcttac taagtgttct gcctgtgggc tatacccctag  11580
ccacctccta ggactttgct gtttatttat ttatttagtt tagggctttg ttattgattt   11640
attagttagt taatttaggg gattaaatga gagagtaatt attacctcat atggtttagc   11700
aactattaca agcatgctag tatcattaat ttgtgggact ctgaattctt tccaaggcaa   11760
gtgtgtgtcc agtattgttc tgggaacccc tccttccctg caggttcata ggagcagagt   11820
ggttttctgg ttgtaaaatc tgccaagaac tggaatgtcc tgtctaggct ctgcatctta   11880
gtgatgggca aaaagatgt agtgtgtgtg acattcatgt ggtggtgcat gcatgtgtgt    11940
acatgagtgt acatgcttga gccctgaaac aggatttctc actcaattgc catcaagctt   12000
tgatgtccct aatccttctc caatactagg ttgtaatagt atacatggca aggctagctt   12060
tttatgtcag ctactgggat tcaaactcag gtctggacag ctgttattgt cagctgagcc   12120
```

-continued

```
ttatctgctg tctttgtcat tatcagctgg gtttaaaaag tatccttgat cctattctca    12180
ccgttcccca aacccaaaca ttcctgggca ccagggttcc aaagcattca gtgtggaacc    12240
aaagtttcag cttccttggc tttgaccaaa gcagtcttgt gcttcacaac tgtcataact    12300
gttgtcaagg gcaacaaagc ctcagggagc agccagatga cctcactccg ttttttggcca   12360
gagacacaaa ctttgcactt gatcttgttt gtgcttttaa gccccgtttt agatgaggtt    12420
cctggaaaag ctaatctcca cgtctttttca tttttctgtt gaacctttcg tgatgctttc   12480
taacttaatt gcaatttaaa aagaggcagc ttgctgtcca ggaggaatga cacaaacact    12540
aggcctctga gtgactaaag accatttgaa atgggtcgtc atctattaca gaaaatgtaa    12600
aatatacttt acacttctta actatgtgcc taaagtatgt tttattttgt tttcctctaa    12660
aaaaagaatt atttatttta cgtatttgag tacactgtag ctgacttcag atccaccaga    12720
agagggcctt agattccatt acagatggtt gtgagctacc gtgtgatggg aattgaactc    12780
aggacctctg gaaagcagt cagtgctctt aaccactgag ccatctttcc ggcctttatt     12840
ttcctttttt taaaaaaaaa ataaatgaaa aattaacttt tatttcatgg gtgtatatat    12900
gtatgggctc aaacatgata tatgtgcatg ggctcacaca tgcagtggtg catgtataaa    12960
agtcagagac aacttgcaga agatggtttg ctcttttcat catatgggcc ctgaggatta    13020
aactcaagtc atcagttttt gtgccaaccc cctttactcc ccgagccttc tctcaacagc    13080
tcctcacttt acctttttat ttaaaaaaca aacaaacaaa caaacaccaa cccagcctcc    13140
cacacaacaa cgaaaagatc tcatgtagcc ccagggtggc tttgaactcc ccatatagct    13200
taggatgact ttgaattcct aatgttcttg cctctacctc ctagttacta tgcctggctt    13260
cttaccatag aatttaagaa attatctaag gtaaagtggg gttatgtgct tataagccag    13320
gcactcagga agaagctaag gcatgatgat tgtgagtttg aagccaaccc aggttacaga    13380
ggatctcatc aagaaatcaa cattcaattt tcaattattt cttaaatttt ttgaggttgg    13440
gctggagggg ttggttaaga gcactggttg gtcttccaga ggacatgagt ttgattccct    13500
gtaccccaca tggtggctca caaccatctg taatttttaat tctagggatc taacgccctc    13560
ttcaagcctt ctcaggcagg tgcataagta cacagtcata catgcacaga aaacacataa    13620
acataaaata aataaattaa aatttttgaaa gttttttttg ggtggaaggt acttttaagt   13680
aacattctat gttatggaac aagtgcattc aatttactta gttttttaat tttagctttt    13740
tgtttgtttg ttttctgttt ggaacaaggt cttgtgtatc ccaagcatcc tcaaagttgt    13800
tgtgtagcga aggatgacct tgaattttt tatactactg ccttcttgag ggcaagcatt     13860
ttaatatagg caaaataaac tttaaacttt gtttgctgtg caggtatata tggtgtgcaa    13920
gtgtatctgt gtgtgtgtgt gtgtgtgtgt gtgtgtgtgt gtgtgagaga gagagagaga    13980
gagagagaga gagagagaga gagagagaga gattagagaa taacttgtgg aagttctctc    14040
cttctaccct gtgggtccca gggtaaactc gggttataag gctttgcacc cttttttccca   14100
ctgagaactt cttgctggcc tcactcccta ttttatttta ttggtggcag tactattgct    14160
tttgaatccc atctgaagct tgttttttgtt gtttggtttt taaggcagtc ttaactgtga   14220
cctaagctgg tttaaaactc acaggaatta tccacctcca cctcccaagt gttgggtta    14280
cagatgtgag ccccaagcct gagtgcttct gaaagctgct tttttttatt tcaaaactat    14340
cttttctctg tgtgtaggtc tgattagttg tggggttagg tggtgtcagc atgatccatc    14400
actctccagc tattattctt aaaatgaagg gtctgggggc tggggattta gctcagtggt    14460
```

-continued

```
agagcgctta cctaggaagc gcaaggccct gggttcggtc cccagctccg aaaaaaagaa   14520
ccaaaaaaaa aaaaaatgaa gggtctggtg gctgaggaaa aagctcagtt gcaaaaaaac   14580
atgaaaacct gattcaatct gtaaagccca cataaaagcc aggcatggcg gcatgcacct   14640
ataaccccag cactggggaa acagaacagg agaataccaa gaacttgctg gtcagtcagt   14700
ctagtttaat tggtgagctc caagctcagt gagaccctgt ctcaaaaata aatggagatg   14760
atctgtcatc aagacctggc ctccatacat atatgcacac atgttactcc ctcacatgaa   14820
acatatttat aaacaaacat atgcacacac ttgtgcatac atgaacagat atctatattg   14880
gcatacacat taaaacacac acacacatat atatatacaa aagtgtgtac aaacataggc   14940
atagtataca accatgcata aatgcacagt cacacatatg aatgcattca tattcacaca   15000
tggacacatg aacacataca tatatgctat atcttatatt acactccatt actatccccc   15060
agtccaggtt tcaaatattt acaaacagaa aagcgggcta ctacctgtac tttttcccaa   15120
ttgcctttga acagcgatct ctcgacacct gatccccgca gtgctccctg cggcagagct   15180
tcatccggaa acaaccccca tgcactctat tgattttaat actggggatt acctggagcc   15240
ttgtaaagct aaacacattg tctactgcta aatacttcat tctttgcccc tttcccatgg   15300
ggcgttttca atccagttat ttttagtgtg ttcttagatt taagcatcca ctagtacaga   15360
ttcaaggata tttttattat cccccaaata acagtatttg ttaggtgtaa ccttgtagtt   15420
tttccccagc ggctaattta aattgctttc atgaatagcc tattctggaa aagtaatttt   15480
tttttttttt tttttttttg ggttcttttt ttcggagctg gggaccgaac ccagggcctt   15540
gcgcttccta ggtaagcgct ctaccactga gctaaatccc cagccccaat tctggacatt   15600
tcttataaat gtcactatgc tgtatgtgtt ctttcagcat tgcaacactt tggttccttt   15660
ttatggctca atactggtct acttatggat ctaccacact atctatccat tcatctcaac   15720
atagtcatgg gtggtatttc tactttgggg ctattataag cttgctagga gtatttatga   15780
ccacatcttt agatgcactg atgcattcat ttatcctaag aacagatcct ggatcatatg   15840
gtggttctgt gttcaaacat cagaggcacc accatttatt ttataatagg catttaagat   15900
ttgggtatct tctaactggg tggtggtggt acatgcctgt agtcccagct cctgggaggc   15960
agaggcaagt agatccgaat tctcgcccta tagtgagtcg tattagtcga c              16011
```